(12) United States Patent
Batch

(10) Patent No.: US 8,020,564 B2
(45) Date of Patent: Sep. 20, 2011

(54) SYSTEM AND METHOD FOR ANALYZING MEDICAL TREATMENT DATA

(75) Inventor: Richard M. Batch, Del Mar, CA (US)

(73) Assignee: CareFusion 303, Inc., San Diego, CA (US)

( * ) Notice: Subject to any disclaimer, the term of this patent is extended or adjusted under 35 U.S.C. 154(b) by 1540 days.

(21) Appl. No.: 10/726,202

(22) Filed: Dec. 1, 2003

(65) Prior Publication Data
US 2005/0119914 A1   Jun. 2, 2005

(51) Int. Cl.
*A61B 19/00* (2006.01)

(52) U.S. Cl. ........................................ 128/897

(58) Field of Classification Search ........... 128/920, 128/891, 921, 922, 923, 924, 897–898; 705/2, 705/3; 600/300–301
See application file for complete search history.

(56) References Cited

U.S. PATENT DOCUMENTS

| | | | |
|---|---|---|---|
| 4,756,706 A | 7/1988 | Kerns | |
| 5,317,506 A * | 5/1994 | Coutre et al. | 604/65 |
| 5,378,231 A | 1/1995 | Johnson et al. | |
| 5,583,758 A * | 12/1996 | McIlroy et al. | 705/2 |
| 5,713,350 A | 2/1998 | Yokota et al. | |
| 5,781,442 A | 7/1998 | Engleson et al. | |
| 5,924,074 A | 7/1999 | Evans | |
| 5,953,704 A | 9/1999 | McIlroy et al. | |
| 6,219,674 B1 | 4/2001 | Classen | |
| 2001/0001144 A1 | 5/2001 | Kapp | |
| 2001/0044731 A1 | 11/2001 | Coffman et al. | |
| 2001/0049608 A1 | 12/2001 | Hochman | |
| 2002/0013551 A1 | 1/2002 | Zaitsu et al. | |
| 2002/0038392 A1 | 3/2002 | De La Huerga | |
| 2002/0099273 A1 * | 7/2002 | Bocionek et al. | 600/300 |
| 2002/0120350 A1 | 8/2002 | Klass et al. | |
| 2002/0143580 A1 | 10/2002 | Bristol et al. | |
| 2003/0014222 A1 | 1/2003 | Klass et al. | |

FOREIGN PATENT DOCUMENTS

| | | |
|---|---|---|
| EP | 1 365 344 A2 | 11/2003 |
| WO | WO 00/78374 A1 | 12/2000 |
| WO | WO 02/099600 A2 | 12/2002 |

* cited by examiner

*Primary Examiner* — Charles A Marmor, II
*Assistant Examiner* — Christine D Hopkins
(74) *Attorney, Agent, or Firm* — McDermott Will & Emery LLP

(57) ABSTRACT

A system and method for compiling and analyzing treatment parameters associated with medical treatments provided to a plurality of patients is provided. A report of the analysis may be provided to a technician or physician for determining medical treatment guidelines representing acceptable values for a selected treatment parameter in accordance with the analysis. The system may further automatically determine medical treatment guidelines and/or adjust preestablished medical treatment guidelines in accordance with the analysis.

21 Claims, 9 Drawing Sheets

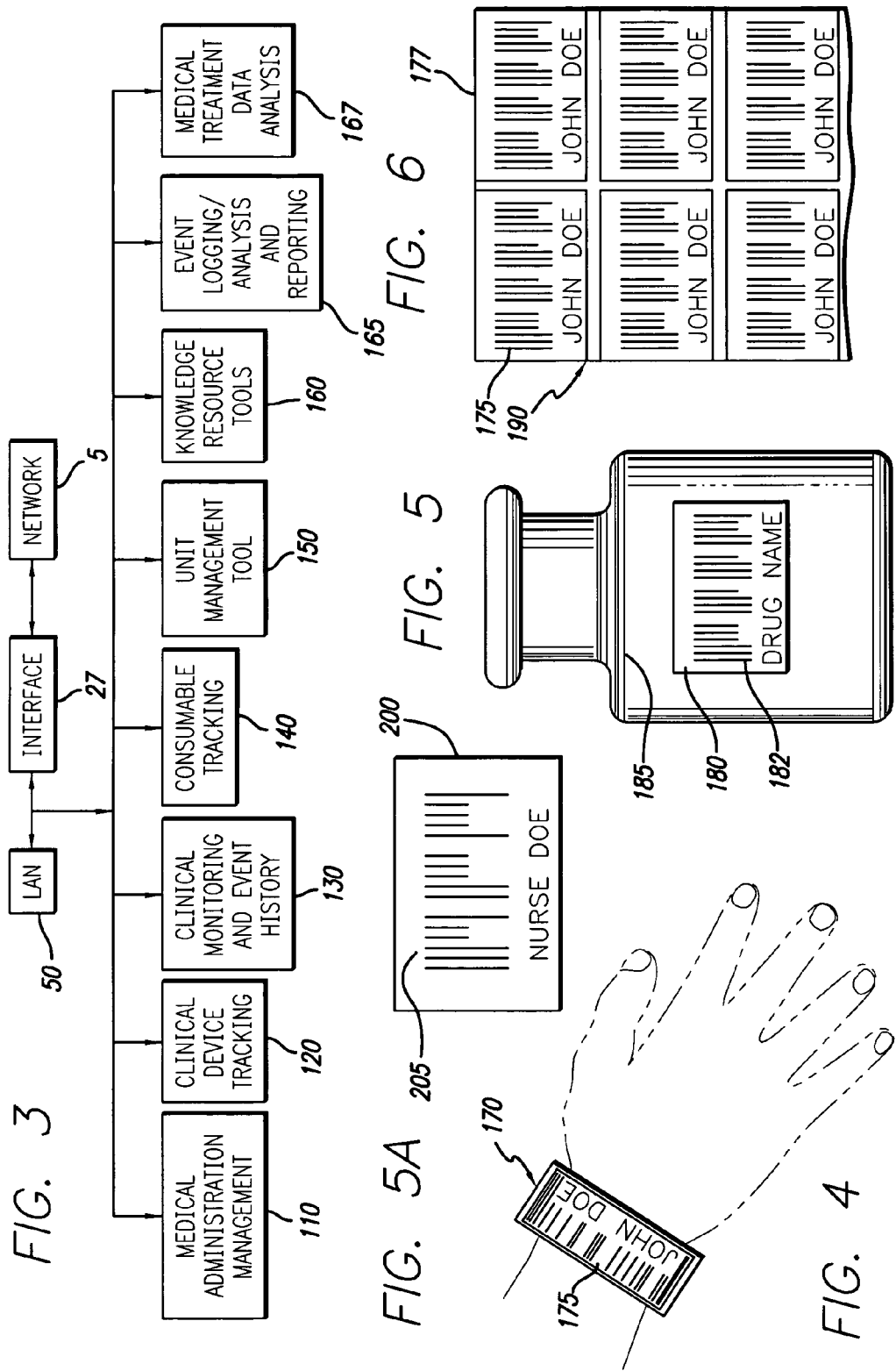

SYSTEM AND METHOD FOR ANALYZING MEDICAL TREATMENT DATA

BACKGROUND OF THE INVENTION

The present invention relates generally to systems and methods for managing patient care in a health care facility, and more particularly, to systems and methods for analyzing medical treatment data to determine institutional guidelines for medical treatments provided to patients.

Medication errors, that is, errors that occur in the ordering, dispensing, and administration of medications, regardless of whether those errors caused injury or not, are a significant consideration in the delivery of healthcare in the institutional setting. Additionally, adverse drug events ("ADE"), which are a subset of medication errors, defined as injuries involving a drug that require medical intervention, and representing some of the most serious medication errors, are responsible for a number of patient injuries and death. Healthcare facilities continually search for ways to reduce the occurrence of medication errors. Various systems and methods are being developed at present to reduce the frequency of occurrence and severity of preventable adverse drug events ("PADE") and other medication errors. In the administration of medication, focus is typically directed to the following five "rights" or factors: the right patient, the right drug, the right route, the right amount, and the right time. Systems and methods seeking to reduce ADE's and PADE's should take these five rights into consideration.

In many hospitals and clinical laboratories, a bracelet device having the patient's identification, such as his or her name printed thereon, is affixed to a patient upon admittance to the facility in order to identify the patient during his or her entire stay. Despite this safeguard, opportunities arise for patient identification error. For example, when a blood sample is taken from a patient, the blood sample must be identified by manually transcribing the patient's name and other information from the patient's identification bracelet. In transferring the patient's name, a nurse or technician may, instead of actually reading the patient's bracelet, miscopy the name or may rely on memory or a different data source. Moreover, manually transferring other information such as parameters for configuring an infusion pump to dispense medication may result in errors that reduce the accuracy and/or effectiveness of drug administration and patient care. This may result in an increased duration of treatment with an attendant increase in cost.

Hospitals and other healthcare institutions continuously strive to provide quality patient care. The possibility of medical errors, such as where the wrong patient receives the wrong drug at the wrong time, in the wrong dosage, or even where the wrong surgery is performed, is a significant concern for all healthcare facilities. Many prescription drugs and injections are identified merely by slips of paper on which the patient's name and identification number have been hand-written by a nurse or technician who is to administer the treatment. For a variety of reasons, such as the transfer of patients to different beds and errors in marking the slips of paper, the possibility arises that a patient may be given an incorrect treatment. This could be prevented by using an automated system to verify that the patient is receiving the correct care. Various solutions to these problems have been proposed, such as systems that use bar codes to identify patients and medications, or systems allowing the bedside entry of patient data. While these systems have advanced the art significantly, even more comprehensive systems could prove to be of greater value.

Delivery, verification, and control of medication in an institutional setting have traditionally been areas where errors can occur. In a typical facility, a physician enters an order for a medication for a particular patient. This order may be handled either as a simple prescription slip, or it may be entered into an automated system, such as a physician order entry ("POE") system. The prescription slip or the electronic prescription from the POE system is routed to the pharmacy, where the order is filled, so that the medication can be provided to the patient. Typically, pharmacies check the physician order against possible allergies of the patient and for possible drug interactions in the case where two or more drugs are prescribed, and also check for contra-indications. Depending on the facility, the medication may be identified and gathered within the pharmacy and placed into a transport carrier for transport to a nurse station. Once at the nurse station, the prescriptions are again checked against the medications that have been identified for delivery to ensure that no errors have occurred.

Typically, medications are delivered to a nurse station in a drug cart or other carrier that allows a certain degree of security to prevent theft or other loss of medications. In one example, the drug cart or carrier is divided into a series of drawers or containers, each container holding the prescribed medication for a single patient. To access the medication, the nurse must enter the appropriate identification to unlock a drawer, door, or container. In other situations, inventories of commonly-used drugs may be placed in a secure cabinet located in an area at or close by a nurse station. This inventory may contain not only topical medications but oral, IM-, and IV-delivered medications as well. Nurse identification and a medication order number are typically required to gain access to the cabinet.

The nurse station receives a listing of drugs to be delivered to patients at intervals throughout the day. A nurse or other care-giver or other qualified person reads the list of medications to be delivered, and gathers those medications from the inventory at the nurse station. Once all of the medications have been gathered for the patients in the unit for which the nurse station is responsible, one or more nurses then take the medications to the individual patients and administer the dosages.

Common to all of these systems is the nurse who delivers the medication. The nurse is central to the process of verifying that the right medication is given to the right patient in the right dosage at the right time at the point of care. No other person in the facility is situated as well as the nurse delivering the medication to ensure or verify that the appropriate drug is being given to the appropriate patient.

Such a system works well to verify that patients are receiving the appropriate drug when drugs are delivered orally, but the system may not be capable of thoroughly verifying that the appropriate medication regimen is being delivered to a patient in the case where IV drugs are being delivered. For example, a nurse may carry an IV bag to a particular patient area, hang the bag, program an infusion pump with appropriate treatment parameters, and begin infusion of the medication. The applicable hospital control system, such as the pharmacy information system, may not know that the patient has received the medication, and if the information is lost somewhere, the possibility exists of medicating the patient twice. Thus, there may be a break in the link of verification that the medication is being properly delivered to the patient if an event occurs resulting in a deviation from the desired treatment parameters.

Moreover, even where the right medication arrives at the right patient for administration, incorrect administration of the medication may occur where the medication is to be administered using an automated or semi-automated administration device, such as an infusion pump, if the automated device is programmed with incorrect medication administration parameters. For example, even where the medication order includes the correct infusion parameters, those parameters may be incorrectly entered into an infusion pump, causing the infusion pump to administer the medication in a manner that may not result in the prescribed treatment.

One attempt at providing a system with built-in safeguards to prevent the incorrect entry of treatment parameters utilizes a customizable drug library which is capable of monitoring the parameter entry process and interacting with the caregiver should an incorrect entry or an out of range entry be attempted. In such a case, an alert is communicated to the care-giver that the parameter entered is either incorrect or out of a range established by the institution where care is being provided. The institutionally established parameters are typically created by polling doctors in the institution as to acceptable entries for the parameters. For instance, doctors may be polled as to the dosage ranges they prescribe for particular drugs. The doctors' input is used as the basis for the institution's customized practice guidelines which are incorporated into the drug library. Even though these customized drug libraries have provided a significant advance in the art for avoiding medication errors, there still exists some inaccuracy in the method used for customizing the dosage limits and other parameters in the drug libraries. Institutionally established guidelines compiled from polling doctors are often not entirely consistent with the actual best practice at the institution, and may result in, for example, dosage range limits that are set too loosely or too tightly compared to the actual best practice. Therefore, it would be advantageous to provide a more accurate system for creating institutional guidelines to ensure medical treatment at the institution is consistent with the actual best practice. It would also be advantageous to provide a system that automatically evaluates and/or adjusts guidelines in accordance with changing best practice procedures over time without requiring further polling of doctors.

Various methods have been used to record all of the activities surrounding the delivery of a treatment regimen, such as providing an infusion pump with a memory dedicated to storing a record of events related to a particular treatment. For example, in one system, an infusion pump has a memory in which treatment information, including treatment parameters, patient identification, care-giver identification and other information are stored for later retrieval. Alternatively, the infusion pump may be programmed to store information related to only certain events occurring during treatment delivery, such as the occurrence of alarms or other alerts. Such systems typically require that the infusion pump be connected to a separate computer using an appropriate communication protocol to query the memory and download a copy of the stored events for analysis. Such information retrieval requires that each infusion pump be connected and analyzed separately, requiring large expenditures of skilled technician time. Additionally, the information retrieved from the memory is generally in a raw form that requires additional analysis before it is useful to an institution to determine safe and effective institutional guidelines or to evaluate preexisting institutional guidelines. Further, the systems that record only errors or particular "events" are not capable of compiling and analyzing data associated with other medical treatments that are consistent with best practice, and thus cannot provide any feedback as to guidelines, rules or limits that are set too loosely and do not generate any errors. These systems also do not automatically analyze the medical treatment data and create, or adjust, guidelines based on the analysis.

There are also systems which expand the customized drug library to include rule sets that represent rules and/or algorithms that modify a parameter based upon data obtained from other sources in the network, such as patient age, body weight, medical history or measurements from vital signs monitoring devices. However, there is no such system that provides rule sets which may be automatically adjusted based on an analysis of actual practice at the institution and trend analysis, and which also takes into account patient outcomes as a result of medical treatments in determining and/or adjusting the rule sets.

Hence what has been recognized as a need, and has heretofore been unavailable, is an integrated, modular system for tracking and controlling patient care which includes the collection and analysis of data relating to medical treatments provided to patients to create and/or adjust institutional guidelines or rules sets for medical treatments to achieve accurate, reliable, efficient, and cost-effective delivery of health care to patients. Such a system would also be capable of sending a report containing the analysis to personnel within the institution for use in updating the guidelines stored in a medical administration device and/or automatically updating preestablished guidelines or rule sets stored in the device. The system would further be capable of taking into account patient outcomes in analyzing the medical treatment data to determine the guidelines or rule sets. The invention fulfills this need and others.

INVENTION SUMMARY

Briefly, and in general terms, the present invention is directed to a new and improved system and method for analyzing the medical treatment of patients in a health care facility. In one aspect, there is provided a system for analyzing medical treatment data associated with medical treatments for a plurality of patients to determine a medical treatment guideline with the system comprising a memory for storing medical treatment data associated with medical treatments for a plurality of patients, the medical treatment data including a plurality of treatment parameters and a treatment parameter value associated with each treatment parameter for each patient, and a processor operatively connected to the memory and configured to compile the medical treatment data according to a selected treatment parameter for a plurality of patients and analyze the treatment parameter values for the selected treatment parameter for determining a medical treatment guideline representing acceptable values for the selected treatment parameter.

In a more detailed aspect, the analysis includes providing a distribution of the treatment parameter values for the selected treatment parameter. Further, the system comprises a database for storing preestablished medication treatment guidelines, and wherein the processor is further configured to compare the treatment parameter values for the selected treatment parameter to the acceptable values for the treatment parameter in the corresponding preestablished medical treatment guideline for the selected parameter. In another aspect, the processor is further configured to adjust the acceptable values for the medical treatment parameter in the preestablished medical treatment guideline as a result of the comparison to create an updated medical treatment guideline for the selected treatment parameter. The processor is further configured to generate a report of the comparison and a report of an analysis.

In yet further aspects, the processor is further configured to determine a medical treatment guideline representing acceptable values for the selected parameter in accordance with the analysis. The processor is further configured to integrate the determined medical treatment guideline into a database of preestablished medical treatment guidelines. The processor is further configured to determine a medical treatment guideline representing an optimum value for the selected parameter in accordance with the analysis.

In another more detailed aspect, the medical treatment data includes patient physiological data, and the processor is further configured to analyze the treatment parameter values of the selected treatment parameter with respect to the corresponding physiological data for each patient and to determine a medical treatment guideline representing at least one optimum value for the selected treatment parameter.

In other aspects, a system for analyzing medical treatment data to determine medical treatment guidelines associated with medication delivered to a patient by a medication administration device is provided with the system comprising a plurality of medication administration devices for delivering medication to a plurality of patients, a memory associated with each medication administration device for storing medical treatment data associated with the medication delivered to each patient, the medical treatment data including patient identification data, medication identification data and medication administration device operating parameters, a central processor configured to receive medical treatment data from each of the medication administration devices, a database operatively connected to the central processor for storing preestablished medical treatment guidelines representing acceptable values for the medical administration device operating parameters, and means for communicating medical treatment data from the medication administration device to the central processor, wherein the processor is configured to compile the medical treatment data according to a selected medication administration device operating parameter for a plurality of patients and analyze the parameter values for the selected medication administration device operating parameter for determining a medical treatment guideline representing acceptable values for the selected parameter.

In a method aspect, a method for analyzing medical treatment data associated with medical treatments for a plurality of patients to determine a medical treatment guideline is provided, the method comprising communicating medical treatment data associated with medical treatments for a plurality of patients, the medical treatment data including a plurality of treatment parameters and a treatment parameter value associated with each treatment parameter for each patient, compiling the medical treatment data according to a selected treatment parameter for a plurality of patients, and analyzing the treatment parameter values for the selected treatment parameter and determining a medical treatment guideline representing acceptable values for the selected treatment parameter.

In more detailed method aspects, the step of analyzing the treatment parameter values includes providing a distribution of the treatment parameter values for the selected treatment parameter. The method further comprises storing preestablished medication treatment guidelines in a database, and comparing the treatment parameter values for the selected treatment parameter to the acceptable values for the treatment parameter in the corresponding preestablished medical treatment guideline for the selected parameter. Further, the method comprises adjusting the acceptable values for the medical treatment parameter in the preestablished medical treatment guideline as a result of the comparison to create an updated medical treatment guideline for the selected treatment parameter.

Other detailed method aspects include generating a report of the comparison and generating a report of the analysis. Also included is the step of determining a medical treatment guideline representing acceptable values for the selected parameter in accordance with the analysis, and integrating the determined medical treatment guideline into a database of preestablished medical treatment guidelines. Further, the step of determining a medical treatment guideline representing an optimum value for the selected parameter in accordance with the analysis is provided.

These and other features and advantages of the invention will become apparent from the following more detailed description when taken in conjunction with the accompanying drawings of illustrative embodiments.

BRIEF DESCRIPTION OF THE DRAWINGS

FIG. 3 is a functional block diagram of the software modules that comprise the care system of FIG. 2;

FIG. 4 is a graphic representation of a patient identification bracelet including a barcode that can be read by a barcode reader;

FIG. 5 is a drawing of a barcode label affixed to a medication container that can be read by a barcode reader;

FIG. 5A is a drawing showing a barcode label affixed to a caregiver identity badge;

FIG. 6 is a drawing showing a sheet of barcode labels that can be affixed to various containers or devices;

DETAILED DESCRIPTION OF THE PREFERRED EMBODIMENTS

The present invention provides a system and method for determining institutional guidelines for medical treatment by collecting and analyzing medical treatment data for patients in a healthcare facility.

Figure 1:
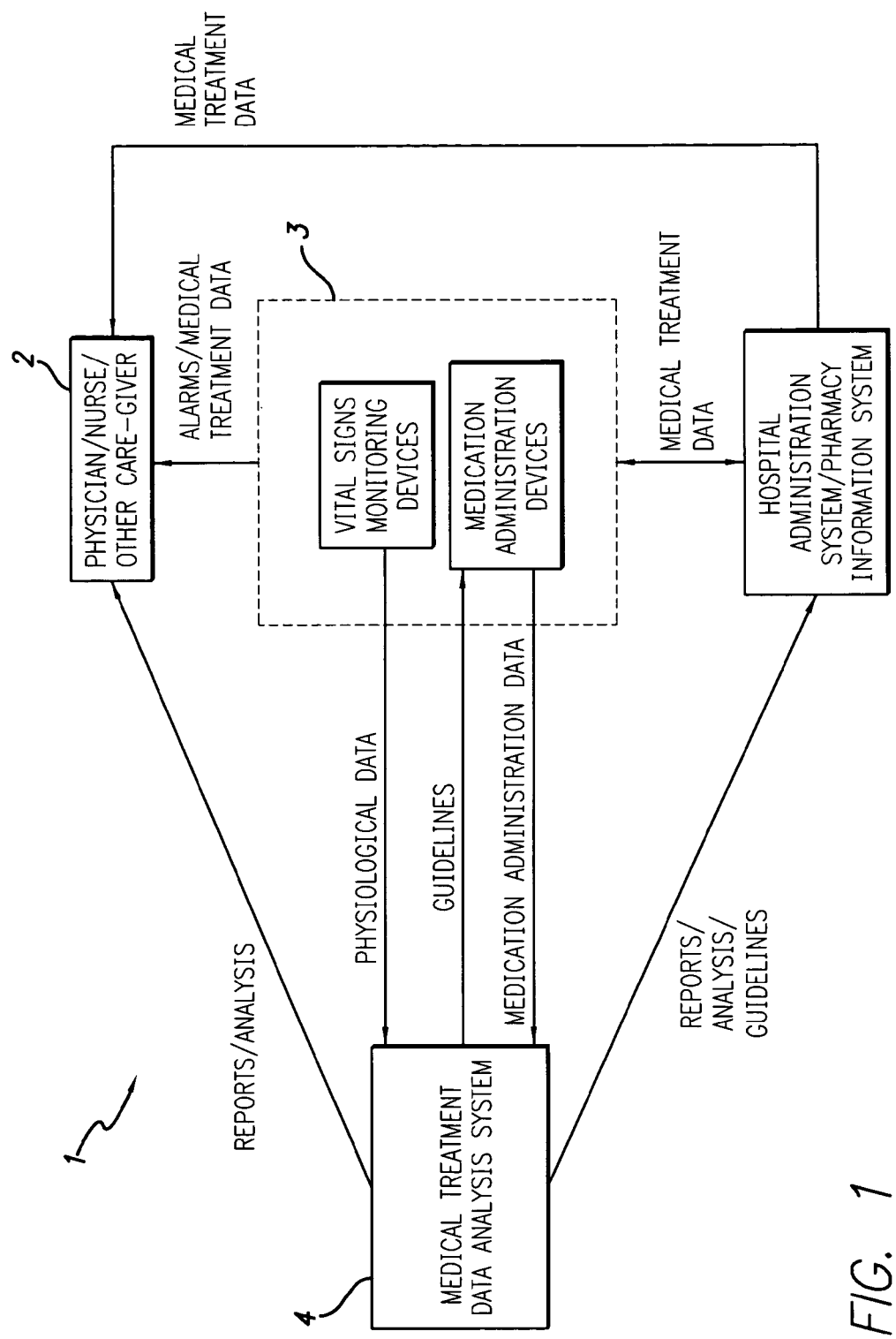
FIG. 1 is a graphical representation of an integrated information and care management system incorporating principles of the present invention and illustrating details of the flow of information within the system.

Referring now to the drawings in which like reference numerals are used to refer to like or corresponding elements among the several figures, there is generally shown in FIG. 1 an integrated hospital-wide information and care management system 1 in accordance with aspects of the present invention. In accordance with the present invention, the information and care management system 1 includes a communications network that ties together various sub-systems at the care giving institution as well as provides for communications to analysis and reporting systems that may be located on-site at the institution, but which may also be located off-site at a location different from the institution.

As shown in FIG. 1, the integrated information and care management system 1 in one embodiment includes a hospital administration system and a pharmacy information system. Medical treatment data, including patient medication information and other non-medication related information, may be entered and stored in the hospital administration system and/or pharmacy information system. Information from these systems, particularly medication information, may be communicated to nurses and care-givers 2, and to the patient's bedside 3. Information generated or collected by various medication administration devices and/or vital signs monitoring devices may be communicated to the hospital administration system and/or pharmacy information system, and alarms or other information may be communicated from the patient's bedside 3 to the nurse or other care-giver 2.

As further depicted in FIG. 1, during or after the administration of medication, information collected from the patient's bedside 3 by medication administration devices and/or vital signs monitoring devices may be communicated to a medical treatment data analysis system 4. Such information may include patient physiological data from vital signs monitoring devices, medication administration data from medication administration devices and any other medical treatment data collected at the patient's bedside 3. This collected medical treatment data may be consolidated for multiple patients and then be analyzed for determining institutional guidelines for medical treatment representing acceptable values or conditions for selected parameters of medical treatment data. The analysis may include, for example, a trend analysis of actual parameter values for a selected treatment parameter for a selected group of patients. Reports of the analysis may be generated on a custom basis, that is, individual reports may be requested, or reports may be generated in a format pre-established by the institution. The reports and analysis may be communicated back to the hospital administration and/or pharmacy information systems, or they may be communicated directly to physicians, nurses or care-givers, or any combination of departments or individuals within the institution that request the reports, or who might benefit from the information and analysis contained within the reports. Additionally, the medical treatment data analysis system 4 may determine new guidelines or adjust preestablished guidelines, which may then be communicated to the pharmacy information or hospital administration systems or to patient bedside devices to update a stored database of preestablished guidelines.

The communications systems connecting each of the hospital administration and pharmacy information systems, the medical treatment data analysis system, the nurse or other care-giver, and the devices at the patient's bedside may be hard wired, wireless, or any combination of both hard wired and wireless elements.

Figure 2:
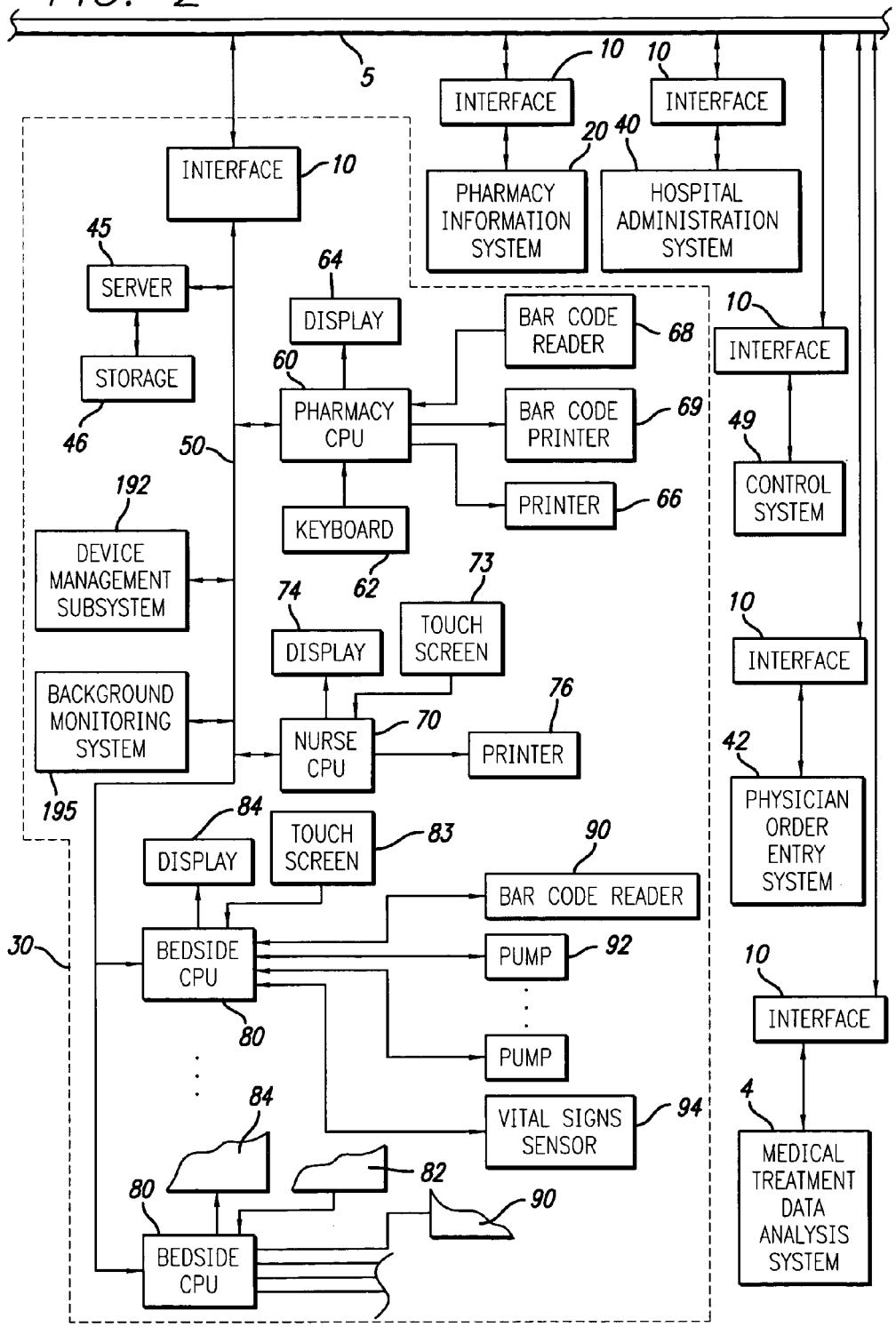
FIG. 2 is functional block diagram of the system of FIG. 1 depicting a care management system and additionally showing an interface with other institutional information systems.

As shown in FIG. 2, various subsystems of a facility's information management system are connected together by way of a communication system 5. The communication system 5 may be, for example, a local area network (LAN), a wide area network (WAN), Internet- or Intranet-based, or some other telecommunications network designed to carry signals allowing communications between the various information systems in the facility. For example, as shown in FIG. 2, the communication system 5 connects, through various interfaces 10, a hospital administration system 40, a pharmacy information system 20, a physician order entry system 42, the medical treatment data analysis system 4, and a control system 49. Also connected to the communication system 5 is a point-of-care management system 30 shown in FIG. 2 as being configured as a local area network 50 with a file server 45 to which are connected a pharmacy computer 60, a nursing station 70, and bedside CPUs 80. The file server 45 stores programs and data input and collected by the various computers in the local area network 50. Various application modules of the patient management system may be resident in each of the computers in the network and will be discussed in more detail below. Ethernet cabling of a local area network 50 is used to connect various CPUs to the file server. The file server 45 also has both local and network hard disk storage for storing programs as well as data gathered on the network. It will be understood by those skilled in the art that all of the ethernet cabling may be replaced using a wireless communication system, as will be described in more detail below.

Each of the various systems 4, 20, 40, 42, and 49 are typically interconnected via a network 5 and appropriate interfaces 10, and generally comprise a combination of hardware such as digital computers which may include one or more central processing units, high speed instruction and data storage, on-line mass storage of operating software and short term storage of data, off-line long-term storage of data, such as removable disk drive platters, CD ROMs, or magnetic tape, and a variety of communication ports for connecting to modems, local or wide area networks, such as the network 5, and printers for generating reports. Such systems may also include remote terminals including video displays and keyboards, touch screens, printers and interfaces to a variety of clinical devices. The processors or CPUs of the various systems are typically controlled by a computer program or programs for carrying out various aspects of the present invention, as will be discussed more fully below, and basic operational software, such as a Windows™ operating system, such as Windows NT™, or Windows 2000™, or Windows XP, distributed by Microsoft, Inc., or another operating program distributed, for example, by Linux, Red Hat, or any other suitable operating system. The operational software will also include various auxiliary programs enabling communications with other hardware or networks, data input and output and report generation and printing, among other functions. Further, while the control system 49 is shown as a separate system in FIG. 2, it will be understood that the control system 49 and the associated mass storage may also be incorporated into another element, such as an infusion pump or other system.

The communication system 5 may comprise, for example, an Ethernet (IEEE 522.3), a token ring network, or other suitable network topology, utilizing either wire or optical telecommunication cabling. In an alternative embodiment, the communication system 5 may comprise a wireless system, utilizing transmitters and receivers positioned throughout the care-giving facility and/or attached to various computers, clinical devices and other equipment used in the facility. In such a wireless system, the signals transmitted and received by the system could be radio frequency (RF), infrared (IR), or other means capable of carrying information in a wireless manner between devices having appropriate transmitters or receivers may be used. It will be immediately understood by those skilled in the art that such a system may be identical to the system set forth in FIG. 2, with the exception that no wires are required to interconnect the various aspects of the system. The LAN 50 may also comprise one of the communications systems described above.

In one embodiment of the present invention, the file server 45 of the care management system is connected by a local area network (LAN) 50 to computers and other peripheral equipment located in the institution's pharmacy, at nursing stations located throughout the institution, and at the patient's bedside. In the embodiment shown, the module located in the pharmacy comprises a central processing unit 60 to which is attached a video display 64 and a keyboard 62 for entry and display of patient information and drug parameters. Also attached to the pharmacy CPU is a bar code reader 68 which is adapted to read barcode labels that may be attached to drug containers, equipment, or caregiver identification badges as will be more fully discussed below. Also connected to the pharmacy CPU 60 is a bar code printer 69 and a printer 66 used for generating reports containing information about patient history and/or patient treatment. The printer 66 may also be used to print barcode labels generated by the pharmacy CPU 60 after patient or drug data is input by a technician or pharmacist into the pharmacy computer 60 using the keyboard 62 or other means.

Another computer, herein referred to as the nursing CPU 70, is located at a nursing station. Nursing stations are typically located in various sections and/or floors of a hospital or clinic and typically provide a central location for record storage and monitoring for a number of patient beds. The nursing CPU 70 located at the nurse station typically includes a video display 74 for displaying patient or other information pertaining to the operation of the particular unit of the institution, and a keyboard 72, mouse, touch screen 73, or other means for entering patient data or specific commands instructing the nursing CPU 70 to generate reports relating to either the patient's medical history or the course and progress of treatment for an individual patient on the attached printer 76 or on the video display 74. As will be discussed more fully below, the nursing station CPU 70 may also generate other reports such as, for example, a printout of drugs scheduled to be administered to patients, productivity measurements such as, for example, the amount of time a nurse spends with a patient or other reports useful for assisting in the efficient operation of the particular unit or the hospital. For example, a report listing the actual times of administration versus the scheduled times for administration may be prepared to assist in evaluation of staffing requirements.

Each care unit associated with the nursing station typically comprises one or more patient beds located in private rooms, shared rooms, or open or semi-open wards that contain multiple beds. In accordance with an embodiment of the present invention, each private room, semi-private room, or ward area has at least one bedside CPU 80 for monitoring and treating one or more patients. Each bedside CPU 80 has a video display 84 and a keyboard 82, mouse, touch screen 83, or other device. The bedside CPU 80 can be used by a nurse, physician, or technician to access a variety of institutional databases to display a variety of information about a particular patient. This information can include an on-line, real-time, graphical patient medication administration record (MAR) that is derived from the patient's medication profile maintained by the hospital's pharmacy information system 20. The bedside CPU 80 also allows remote access to a patient's records stored by the file server 45 to display medication history for the patient. This medication history includes a listing of all drug or other treatments including past, present and future deliveries to the patient. Additionally, access to administration records of the hospital's administration system 40 is available through the network 5. Alternatively, this information may also be stored, as will be discussed in more detail below, in a medication database carrier, the pharmacy information system, or a separate system dedicated to collecting, analyzing and producing reports concerning medical treatment data for determining institutional guidelines or concerning various alerts or clinical "events" that are recorded or logged during the administration of medical treatment to a patient.

In one embodiment of the present invention, the bedside CPU further includes a database including a library or libraries of information concerning past and present medical administration activities and/or institutional guidelines for appropriate parameters for administration of various medications. For example, the guidelines may include institutionally established guidelines or limits on drug administration parameters, such as dosage, frequency of administration, and other delivery related information such as, for example, appropriate flow rates and infusion durations for programming infusion pumps. Additionally, the guidelines may encompass guidelines for providing drug administration appropriate to particular patient treatment areas having different sets of delivery parameters for similar medications, such as medication administration directed to geriatric, pediatric and oncology patients. Guidelines may also be included that are directed to particular therapy regimens, such as chemotherapy regimens or regimens for treating chronic infection or pain. The guidelines library stored in the bedside CPUs may be accessible by the medication administration devices during programming of an infusion. Alternatively, the database of libraries may be stored directly in the medication administration device or another computer connected to the network and accessible by the medication administration device.

Each bedside CPU 80 can be connected through an appropriate interface to a variety of peripheral equipment. For example, a barcode reader 90 capable of reading barcodes on a patient's wristband or medication container; a medication administration device, such as infusion pump 92, for delivering medication to the patient in a predetermined, controlled manner; or various sensors 94 that can automatically monitor a patient's vital signs and send signals representative of these vital signs to the computer through an appropriate interface for storage and later retrieval by a selected software application to provide a graphic display of the patient's vital signs during the course of treatment.

A plurality of bedside CPUs are shown in the drawing; however, more or fewer may exist depending on the particular system and hospital requirements.

Referring now to FIG. 3, a block diagram illustrating the various application software modules comprising an illustrative embodiment of the care management system of the present invention is shown. The care management system's application software is modular in construction to allow installation and operation of the system with only one or more of the application software groups present. This provides flexibility in meeting the widely varying needs of individual institutions where cost and complexity may be an issue or where the full system is not needed. Each of the modular applications, however, is fully integratable into the system.

The programs of the care management system control alarms or alerts generated by one of the modular applications. Alarms are routed automatically to the appropriate video display. For example, an occlusion alarm generated by a pump 92 may remain local for a predetermined period. After that period the patient's bedside computer 80 may then broadcast the alarm by causing the alarm to be communicated over the LAN 50 to alert other hospital staff of a potential problem or to cause a particular person responsible for the care of a patient, such as, for example, a physician or nurse, to be paged.

Each of the modular applications will now be described in detail. The operation of each of these modular applications in a clinical setting will be discussed more fully below. The medical administration management module 110 integrates medical order information, infusion pump monitoring, and barcode technology to support the real-time verification and charting of medications being administered to a patient. The medical administration management module 110 creates and maintains an on-line, real-time, patient-specific medication administration record ("MAR") or integrated medication administration record ("IMAR") for each patient. This medication administration module 110 contains all of the information generated in the institution regarding the care provided to the patient. The medication administration management module 110 gathers information from the various nursing and bedside CPU's 70, 80 (FIG. 1) comprising the peripheral hardware of the care management system 30 that is distributed throughout the institution. For example, when a physician attending a patient diagnoses an illness and determines an appropriate course of treatment for the patient, the physician may prepare a handwritten medical order specifying the desired therapeutic treatment as well as any appropriate parameters such as dosage and/or period of administration. The written prescription is sent through the institutional mail system to the pharmacy where it is then entered into the pharmacy information system 20 through a dedicated terminal, or other means, and is then entered into the care management system.

In another embodiment, the physician accesses the pharmacy information system 20 through a dedicated terminal or through the care management system 30 via the network 5 using either a nursing CPU 70 or a bedside CPU 80. Alternatively, the treatment order may be entered by a nurse or other qualified caregiver into either the pharmacy information system 20 or the care management system 30.

Referring now to FIGS. 4-6, a variety of implementations of the barcode identification system that may be used with the present invention are shown. FIG. 4, for example, shows a patient identification bracelet 170 of the kind typically used in hospitals and other institutional settings to ensure that each patient is able to be identified even if the patient is unconscious or otherwise unable to respond to questioning. A barcode 175 is printed on a label that is attached to the patient identification bracelet 170 and has encoded within its sequence of bars the information necessary to identify the patient. This barcode may be read using a computerized barcode reader 68, 90, such as those shown connected to the pharmacy CPU 60 and the bedside CPUs 80 (FIG. 1). The barcode reader comprises a light emitting and receiving wand 95 that scans across the barcode. The light emitted by the wand 95 is reflected by the sequence of dark and light lines comprising the barcode into the receiving lens of the wand 95. A sensor in the wand 95 converts the received light into a signal that is then transmitted to the CPU. A software application program running on the CPU then decodes the signal into the data represented by the barcode in a manner well known to one skilled in the art. Using appropriate software programs, this data may then be automatically entered into a database stored in the CPU's memory or disk storage. While a barcode has been described for purposes of illustration, those skilled in the art will immediately understand that other systems, such as magnetic stripes, or programmed punched holes may also be used to represent data stored on each label, care giver badge or patient wrist band.

Barcode systems are extremely flexible and the amount of information that can be represented by the barcode, while limited, can be used in a variety of ways. For example, as depicted in FIG. 5, a drug container 185 is identified by a label 180 having a barcode 182 printed thereon. This barcode 182 can represent the patient identification and the medical order number, and any other information the institution finds helpful in dispensing the drug and tracking the treatment. The barcode 182 may also be read using a barcode reader, and, using suitable application software such as that included within the medical administration management module 110, discussed below, can be used to link the drug container and its contents with the patient identification bracelet 170 affixed to a patient to ensure the right drug is delivered to the right patient at the right time in the right manner. The use of barcodes is not limited to the implementations discussed above. A sheet 190 of barcode labels 177 having barcodes 175 is shown in FIG. 6. Such labels can be printed by a printer connected to the pharmacy CPU 60 of the care management system 30 or, alternatively, by any other printer connected to any other hospital information system that can be programmed to produce barcodes bearing the information in a form that can be read by the barcode readers connected to the various CPUs of the care management system. These barcode labels 177 may then be affixed to clinical devices, patient belongings, or other items where positive identification is needed.

Alternatively, other devices may be affixed to the patient, drug, nurse or medical device that may communicate with the care management system using wireless means. For example, IR or RF transceivers may be incorporated into medication database carriers or other identification devices that are capable of interfacing and communicating with the care management system. Other wireless technologies may also be used.

Figure 7:
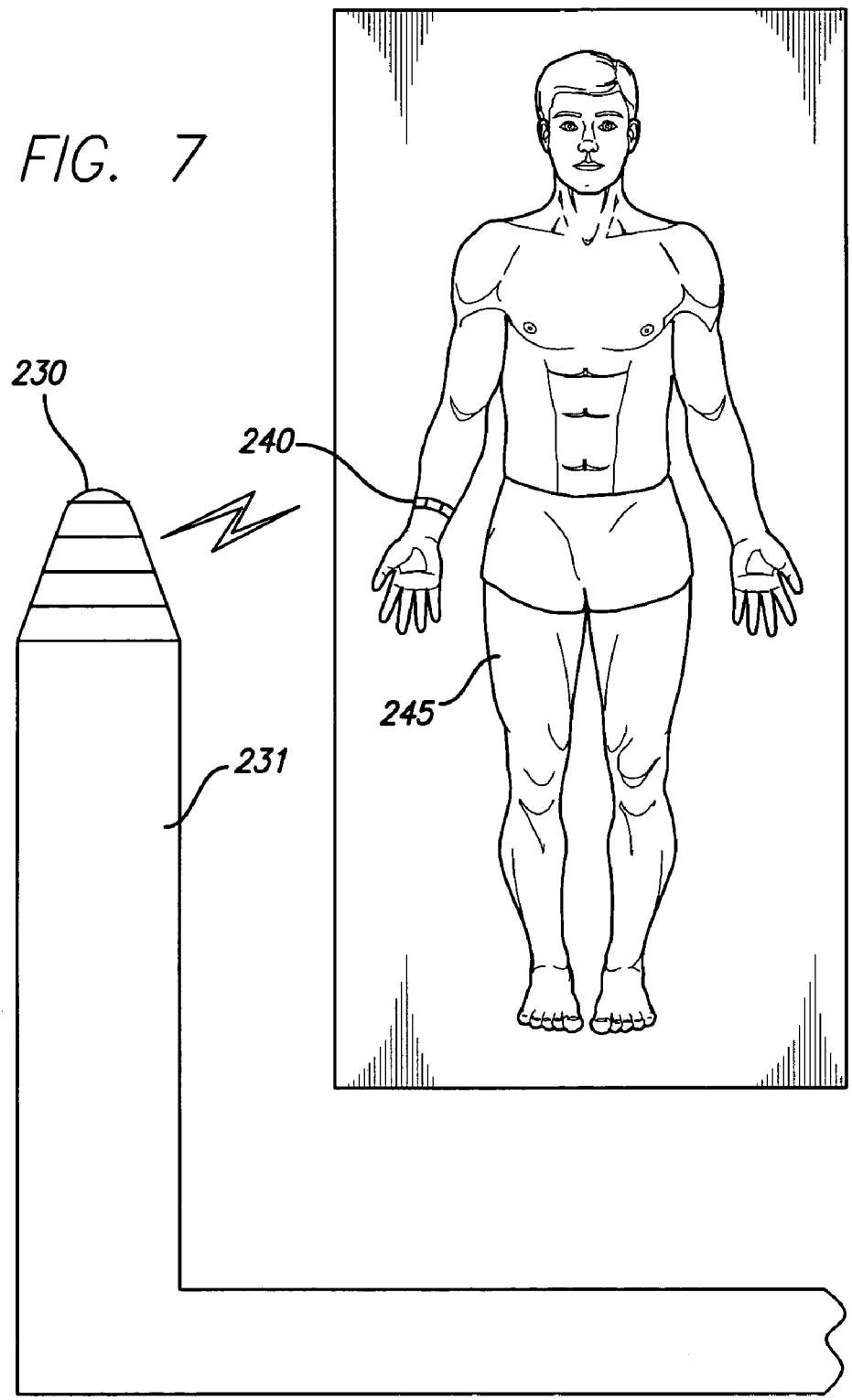
FIG. 7 presents a view of a patient having an identification device located on his arm that interacts with a transmitter/receiver located in the frame of the entry/exit of the room in which the patient is located. The identification device and transmitter/receiver form a passive identification system in accordance with an aspect of the invention.

Another embodiment of the care management system is shown in FIG. 7 wherein the patient 245 and/or caregiver have badges or wrist bands 240 or other devices suitable for attachment to a person's body or clothing that may also include electronic circuitry that is responsive to signals from a transmitter/receiver 230 located in each patient room or treatment area to automatically provide the care management system (FIG. 2) with the identity of, and possibly other selected information about, the occupants of the patient room or treatment area, eliminating the need to use a bar-code reader to read the bar-codes on the patient and/or caregiver badges or wrist bands. Such a system may be described as a passive recognition system in that neither the patient nor the caregiver need take any active steps to inform the care management system of their location within the institution.

One example of such a system incorporates an intelligent RF computer chip into the caregiver or patient badge or wristband 240 that provides a unique, or programmed response with a passive RF transponder 230 located within a patient room or treatment area, such as in the frame 231 of the entry or exit of the room or treatment area, or mounted on a wall or ceiling. Each badge or wrist band 240 interacts with signals of the transponder 230 in a unique way, the unique interaction representing an assigned code for the badge or wristband 240. Utilizing this technology would remove manual steps and some of the "human factor" from the process of identifying the patient and caregiver.

When an individual 245 wearing a badge or wristband 240 having such a circuit enters a room or area where a transmitter/receiver 230 is located, the electronic circuit in the badge or wristband 240 interacts with signals emitted by the transmitter without any positive action on the part of the caregiver or the patient. This interaction may be sensed by the receiver, which may be capable of determining the identity of the badge or wristband 240 from the interaction of the electronic circuit with the emitted signals. Alternatively, the receiver may simply sense the interaction and provide a signal representative of the sensed interaction to a computer or other processor that has been programmed or otherwise configured to determine the identity of the individual associated with that particular badge or wristband 240.

Although the preceding paragraphs describe a passive recognition system using electrical circuitry, other approaches may also be used. For example, it can be envisioned that the patient and/or caregiver may have magnetically-encoded devices that can be automatically read by an appropriate detector located in the patient room or treatment area.

One of the key advantages of the medical administration management module 110 (FIG. 3) is that the module works in concert with the barcode labels or wire-less identification devices described above. When the medication administration management module 110 is implemented using the hardware system described above comprising a pharmacy CPU 60, barcode reader 68, and printer 66, together with a bedside CPU 80 with a connected barcode reader 90, the care management system ensures that medication is administered to the right patient, in the right dose, along the right route and at the right time.

Because the medication administration management module 110 maintains an on-line, real-time, patient specific graphical medication administration record that includes both past, present and future scheduled medications, a nurse may select a scheduled dosage on the MAR and indicate that it will not be administered for specified reasons selected from a list of options that are dependant upon the health status of the patient at a particular time. This system also allows a nurse to select a scheduled dose on the MAR, and record notes and observations about the dose selected from a list of options. The medical administration management module 110 also provides on-line, real-time help screens that can be accessed by a nurse or other caregiver to display specific information about selected medication and dose to be dispensed.

The medication administration management module 110 provides a list of on-going infusions that can be displayed on the video display of the pharmacy CPU 60. Drug administrations that will terminate within a preselected time period may be distinguished from other administrations by color highlighting or other means. The time remaining, drug, and patient name are presented as well as buttons for program control.

The medication administration module 110 records and maintains in a stored file a log of alerts that are generated when any discrepancy is identified, for example, during the verification process which will be discussed more fully below. The medication administration module 110 also allows the nurse to acknowledge and correct the discrepancy in real-time, or override the alert by entering the appropriate command. Even where the nurse is allowed to override the alert, the medication administration application module 110 prompts the nurse for a reason for each alert override and then automatically enters the reason into the MAR for the patient.

The medication administration module may also be capable of compiling and analyzing medical treatment data for a plurality of patients, either hospital-wide or for specific hospital areas, and determining medical treatment guidelines in accordance with the analysis. In another embodiment, as will be described in more detail below, such analysis and guideline determination may be provided by a separate system. Similarly, the medication administration module may also be capable of tracking specific alert conditions that are reported by specific medication administration devices indicating that particular treatment parameters have not been correctly entered into the device by a caregiver. These alerts, or "events" may be either automatically stored in a database associated with the medication administration module 110, or, as will be described more fully below, may be stored in a dedicated event logging/analysis and reporting server. The analysis may generate reports for a specified medication administration device or the analysis may consolidate event reports from all, or a selected subset of, the medication administration devices in an institution, and may provide reports in accordance with either customized formats or formats pre-established by the institution.

The clinical monitoring and event history module 130 shown in FIG. 3 is designed to monitor a variety of clinical devices attached to the network in a real-time manner and provides information about those devices to monitoring stations located elsewhere on the network. For example, the clinical monitoring and event history module 130 can be configured to monitor a plurality of clinical devices that are in use to deliver medication to patients in the private rooms, semi-private rooms or ward areas in a nursing unit. The clinical monitoring and event history module 130 retrieves real-time data from each device, and displays a visual representation of each device including all significant data related to its status and settings on the video display 74 connected to the Nursing CPU 70 (FIG. 2). For example, in the case where the clinical monitoring and event history module 130 is monitoring an infusion pump 92, a nurse at the nursing station can access the status for that pump wherein the display 74 attached to the nurse CPU 70 then displays information regarding the status of the infusion being performed at that time. For example, information can include the name of the drug being infused, the patient's name, the scheduled start, the actual start of infusion, the scheduled end of infusion, the projected end of infusion, the amount of drug infused, the amount of drug remaining to be infused and any alert or discrepancy conditions that may need attention by the nurse. Because the care management system is a fully integrated system, the medical administration management module 110 works in concert with the clinical monitoring and event history module 130 so that a nurse, doctor or technician may, after evaluating the status of the infusion displayed on either the video display 74 at the nursing CPU 70 or on the video display 84 at the bedside CPU 80 may, by using the touch screen 73, 83 of the computer, adjust the infusion regimen accordingly using, for example, a screen displayed on the video display 74, 84.

The clinical monitoring event history module 130 may also be programmed to immediately display alarm conditions on remote monitoring screens, such as the video display 74 attached to the nursing CPU 70, as the alarm occurs. For example, the status of each patient's infusion can be represented on a video display at the nursing station. When an alert occurs, the box representing the patient's room flashes red to attract attention to the alert. Displaying the alarm condition in this manner allows a nurse to quickly and easily identify the patient from the nursing station and take appropriate action to address the condition causing the alarm. The system may also be programmed to display certain alarms that have been identified as particularly important events at other video displays located throughout the institution, such as the video display 64 attached to the pharmacy CPU 60 located in the institution's pharmacy.

Additionally, the clinical monitoring module 130 may be interfaced through appropriate communications means (wired or wireless) with a variety of patient vital signs monitoring devices and laboratory and diagnostic equipment. In this embodiment, information about the patient's vital signs, laboratory tests, etc. may be captured, such as stored in a memory, and be available for analysis and correlation with the patient's treatment history. In this way, an individual patient treatment history may be analyzed, closing the loop between treatment variables and patient outcome after treatment may be determined. Additionally, and which will be discussed in more detail below, the institution may analyze outcomes over many patients to determine the best practices for particular drugs or treatment regimens that should be used in the institution.

The clinical device tracking and reporting module 120 shown in FIG. 3 is used to maintain a record of the location of each clinical device and the history of its use in the institution. This system maintains a record of the current or last known location within the institution of each clinical device used in the institution, such as an infusion pump or vital sign sensor. Thus, the appropriate equipment can be easily located by a nurse or a technician for a given therapy regimen or vital sign measurement. This is particularly useful in a large hospital or clinic having many patient rooms, patient beds, or treatment areas where equipment may be temporarily misplaced. This system is also useful in those particular instances where an emergency occurs where treatment requires a particular piece of equipment. The status of that equipment can be easily ascertained from a remote video terminal, such as the video display 74 connected to the nursing CPU 70.

The clinical device tracking and reporting module 120 also maintains a record containing the usage history of each clinical device, including information about the patient it was used to treat, its location, the date, time, duration of use, any alarms that occurred and what medications were dispensed. This history may also contain the maintenance and calibration records for a clinical device. Such information can be queried on-line by technicians, nurses or other hospital administration personnel to generate reports to assist in locating the clinical device, report on the historical usage of the device, and to provide a log of preventative maintenance and equipment calibration. The efficient calibration of complex and sensitive clinical devices is particularly important in a heath care institution to maintain accuracy and quality of therapeutic treatment delivery. Maintaining a history of the usage of the device is also helpful to justify purchasing additional clinical devices when needed, or where the record indicates that a particular clinical device has become obsolete and needs to be replaced by a newer model of the device.

The care management system may also include a consumable tracking module 140 that maintains a record of all consumable item usage for treatment of each patient. This record ensures that appropriate supplies are ordered and delivered to the nursing unit in a timely and cost-efficient manner to prevent outages of necessary supplies. Such information may also be used by the hospital inventory systems through an appropriate interface or other management system to ensure that the supply purchasing is done as cost-effectively as possible. The consumable tracking module 140 provides on-line queries and report generation summarizing consumable uses for a particular patient, a particular nursing unit, or a variety of other purposes.

The unit management tool module 150 assists nurses in sharing information related to patients and automates routine transactions within the nursing unit. The unit management tool module 150 allows a nurse to record the allergies, handicaps, and special care needs of the patient which, cooperating with the medication administration record module 110 and the clinical monitoring and event history module 130, displays that information prominently on all appropriate display screens, either at the pharmacy video display 64, the nursing video display 74 or at the bedside video display 84 (FIG. 2). The unit management tools module 150 also allows a nurse to record patient transfers and the times when the patient is out of the room or off the floor, such as, for example, when the patient is transferred to surgery or to a different part of the institution for a particular kind of treatment such as rehabilitative therapy. This system may also be programmed to signal an alarm when a patient has been disconnected from the system longer than scheduled, for example, when the patient disconnects from the infusion to attend to personal hygiene. This function ensures that an alarm or alert is sounded and that appropriate personnel are notified of any potential problems and can take the necessary actions to alleviate the alert condition.

The knowledge resource tools module 160 provides a framework for information sharing among the various units in the hospital and also supports an assortment of everyday tools used by the nurses, physicians and technicians involved in the delivery of health care within the institution. This module allows or assists in integrating external information sources into the care system to improve the effectiveness of the care management team in treating the patients in the institution.

For example, the knowledge resource tools module 160 may provide a variety of on-line tools including, for example, a calculator, a dose rate calculator for calculating the appropriate dosage and infusion rate for a particular drug to be infused into a patient, a standard measurement conversion calculator for converting between units of measurement, a body surface area calculator, and a timer and stopwatch. These resources may be displayed on the video displays 64, 74, 84 at appropriate points within the system, and are available from any CPU either in the pharmacy, at the nursing station or at the bedside. These application tools can be programmed to appear on the video display 64, 74, 84 either automatically, such as, for example, when an infusion pump is configured at the start of an infusion to assist in the calculation of a dose rate. These resources may also be available upon entry of the appropriate command by a nurse, physician or technician.

In accordance with the present invention, one or more separate modules may monitor, manage and/or update the institutional guidelines for medical treatments stored in a database at the bedside CPU 80, medication administration device or other location in the institution. As mentioned previously, the medication administration module 110 may alternatively perform these functions instead of a separate module. Medical treatment guidelines, as discussed above, provide appropriate parameters for administration of various medications or other medical treatments. The guidelines are typically accessed during initiation of a medical treatment to verify that the parameters of the medical treatment fall within the acceptable guidelines, and an alert may be provided to indicate an incorrect or out of range parameter value.

One embodiment of the care management system may include an event logging/analysis and reporting module 165, as depicted in FIG. 3. This module may be implemented in a variety of ways. For example, the event logging system 165 may be part of an institution's medication administration management module 110, it may be a separate module 165 as shown, or it may be implemented in a different computer system, which may or may not be located in the institution. For example, in one embodiment, event logging/analysis and reporting module 165 may be resident on a third party computer system located outside of the institution, but in communication with the institution's systems using a wired or wireless, or combination of both, communication system. The event logging module may also be incorporated into the medical treatment data module 167, discussed in more detail below.

A common feature of the various configurations of the event logging/analysis and reporting module 165 is that the module receives, or retrieves, information from medication administration devices related to alarms or alerts generated by the medication administration device before or during administration of medical treatments to a patient, analyzes the information, and then provides reports related to the received or retrieved information to the institution. These reports may be used by the institution to improve the delivery of medication to patients in the institution, by identifying frequently occurring errors or conditions that can be corrected through improvements to the medication delivery process or training or caregivers. Such reports may either be customized on demand, that is, a caregiver or other individual responsible for analyzing the events may request a custom report, or the system may provide a menu of reporting formats pre-established by the institution that may be selected by the individual or department requesting the report. Alternatively, the system may be automated so that reports in pre-established formats are produced and distributed to appropriate individuals or departments in the institution at pre-selected intervals. Such a system will typically be embodied in one or more databases stored in a memory from which event related information may be extracted and analyzed using a processor controlled by an appropriate software program. The results of the analysis may be stored in a memory for future use or distribution, or may be printed using a printer.

The medical treatment data analysis module 167 is used to review the analysis of medical treatment data and receive medical treatment guidelines determined in accordance with the analysis. In one embodiment, the storage and the analysis of the medical treatment data occurs in a separate medical treatment data analysis system 4 (FIG. 2) that communicates with the module 167 in the care management system. The module 167 is designed to provide a user interface for the medical treatment analysis system 4 at the point-of-care and to receive, or retrieve, medical treatment guidelines determined by the system for incorporation into a database of such guidelines stored in the point-of-care management system. In an alternative embodiment, the module 167 may encompass the entire medical treatment data analysis system and be run from one of the CPUs of the care management system, instead of from a separate system as shown in FIG. 2. The medical treatment data analysis module 167 may also be part of an institution's medication administration management module 110 or clinical monitoring module 130, rather than a separate module 167 as shown.

Medical treatment data includes patient identification data and other patient-specific information, medication identification data and parameters for various medical treatments, including the administration of medication delivered to a patient by a medication administration device. The treatment parameters for a medication administration, for example, would include medication administration device operating parameters, such as dosage, frequency of administration, flow rates, and infusion duration. Treatment parameters may also comprise physiological parameters as measured by vital signs monitoring devices, other sensors or laboratory tests.

Figure 8:
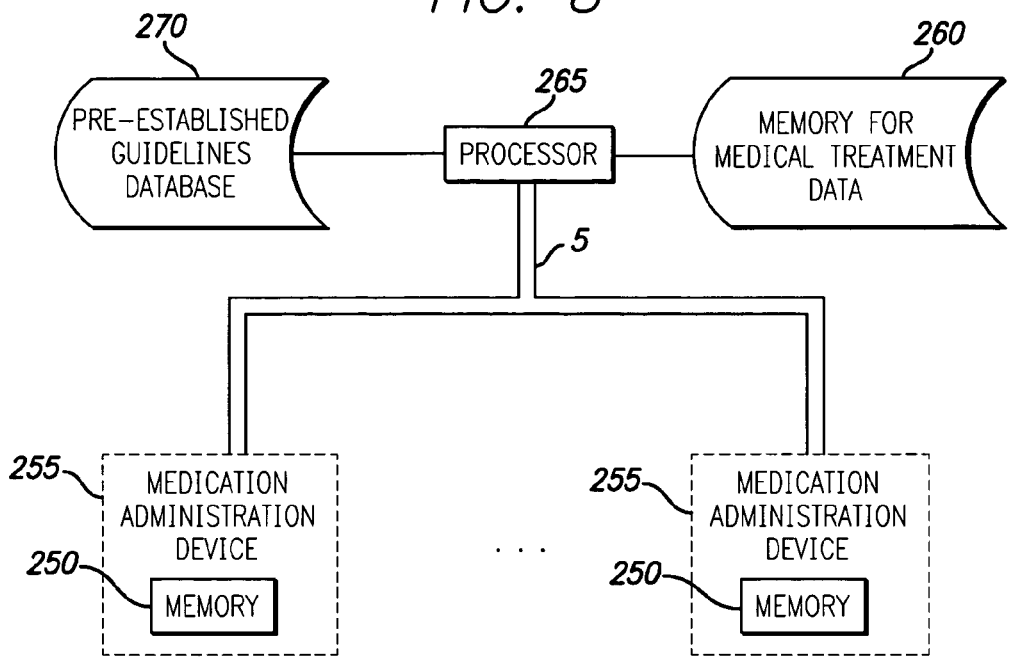
FIG. 8 is a functional block diagram of the components of a medical treatment data analysis system in accordance with the present invention.

Referring now to FIG. 8, the medical treatment data may be communicated via network 5 from a memory 250 of a medication administration device 255, either directly or via a bedside CPU (FIG. 2) or other computer connected to the network. The data may be collected in real-time from the devices as infusions are initiated or modified. Alternatively, the data may be transferred from the devices in batch mode at selected intervals. Medical treatment data may also be collected from the hospital administration system or pharmacy information system or other system or CPU where such information is stored. For example, in the case where prescription information for medication to be administered is entered into the pharmacy information system, such information may be communicated directly to the medical treatment data analysis system, rather than from the medication administration device. Other information stored in the hospital administration system or pharmacy information system may additionally be communicated to the analysis system.

Figure 9:
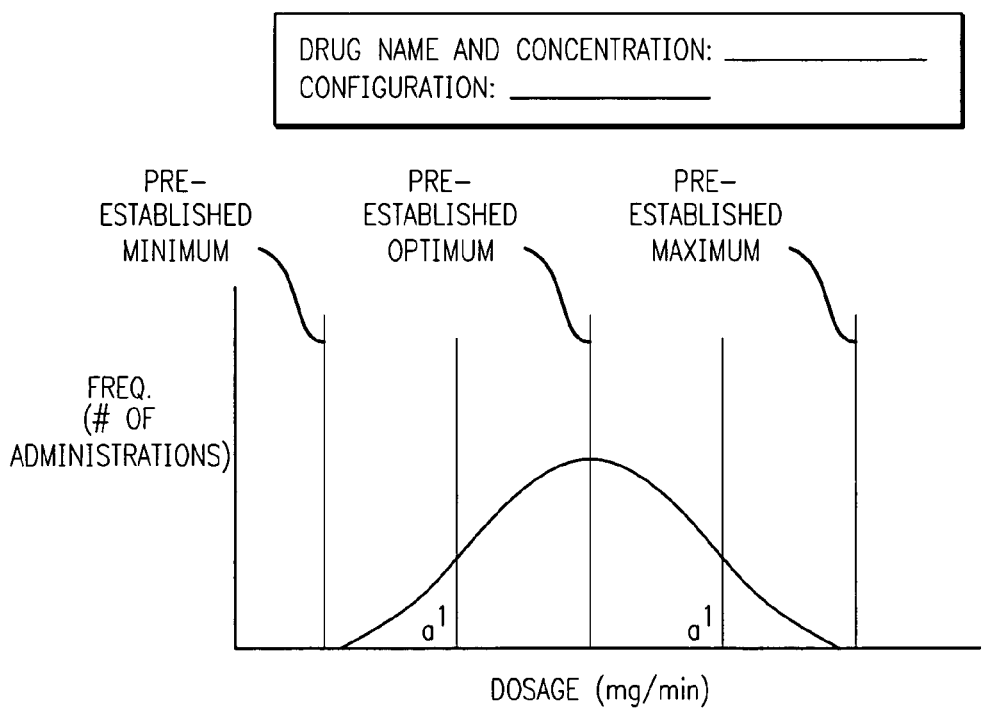
FIG. 9 is graph of the dosage of a medication as a function of the frequency of administration of the dosage and further showing preestablished guidelines for acceptable dosages of the medication.

As shown in FIG. 8, a memory 260 associated with the medical treatment data analysis system 4 may store the collected medical treatment data. A central processor 265 operatively connected to the memory compiles the data according to a selected treatment parameter for a plurality of patients, either hospital-wide or for a particular patient treatment area. For example, the medical treatment data may be collected for geriatric, pediatric, ICU or oncology patients. The processor further analyzes the treatment parameter values for the selected treatment parameter for determining a medical treatment guideline representing acceptable values for the selected treatment parameter in accordance with the analysis. In one embodiment, for example, the analysis includes providing a distribution or statistical or trend analysis of the treatment parameter values for the selected treatment parameter. Such analysis reveals trends or patterns of practice at the institution for the various medical treatments to aid in determining practice guidelines. For example, the graph of FIG. 9 shows dosage values of a particular medication as a function of the frequency the dosage is administered. Analysis of data taken from the records of many treatments may reveal that, for example, as shown on the graph, ninety percent of all dosages given fall with the area under the curve bounded by the lines labeled a'. Accordingly, the institution may adjust the preexistent minimum and maximum bounds to the lines indicated by a', thus tightening the range of permissible dosages allowed. When a dosage is prescribed or attempted to be administered that falls beyond the new limits, as depicted by lines a', then an alert is provided to the care-giver, and the occurrence of the out-of-limit event is stored for reporting and analysis.

Reports of the analysis may be generated on a customized basis or in a format pre-established by the institution. The reports and analysis may be communicated back to the hospital administration and/or pharmacy information systems, or they may be communicated directly to technicians, physicians, nurses or care-givers, or any combination of departments or individuals within the institution that request the reports, for review in determining institutional guidelines for medical treatments.

The medical treatment data analysis system may further determine a medical treatment guideline representing acceptable values or an optimum value for the selected parameter in accordance with the analysis. The determined guidelines may be presented in a report to technicians or physicians for their review and/or approval. In one embodiment, the determined guidelines may be automatically integrated into a database of medical treatment guidelines. The database may be stored in a medication administration device or an associated bedside CPU. Alternatively, the determined guidelines may be sent to the hospital administration system or pharmacy information system or another computer that stores the guidelines database.

As part of the analysis, the treatment parameter values for the selected treatment parameter may be compared to the acceptable values for the treatment parameter in a preestablished medical treatment guideline already present in a guidelines database 270. As shown in FIG. 9, the curve representing the pattern of practice for the dosing of the particular medication is compared to a preestablished dosage guideline including minimum and maximum acceptable values and an optimum value. The processor may further automatically adjust the acceptable values for the medical treatment parameter in the preestablished medical treatment guideline as a result of the comparison to create an updated medical treatment guideline for the selected treatment parameter.

In determining optimum values for a selected treatment parameter, the system may further integrate physiological data and other patient data associated with a patient and evaluate the selected treatment parameter value received by the patient on the basis of the physiological and other patient data. Such an evaluation ties in the actual clinical outcome associated with a treatment parameter value to more accurately determine optimum guidelines for the treatment parameter. The physiological and other patient data may also be used in analyzing and determining rule sets that represent rules and/or algorithms that modify a treatment parameter based upon such data. For example, the medical treatment guidelines may include a rule that limits the dosage of a particular drug when the patient's blood pressure falls below a threshold. The medical treatment data analysis system may analyze the actual dosages prescribed for that drug at the institution as a function of blood pressure and compare it to the preestablished rule in order to determine whether the rule is consistent with the actual practice at the institution. Other physiological data from vital signs monitoring device or laboratory tests that are indicative of patient outcome may also be taken into account in determining and/or adjusting the rule sets.

The system 4 may determine guidelines for a variety of treatment parameters. For example, the guidelines may encompass guidelines for providing drug administration appropriate to particular patient treatment areas having different sets of delivery parameters for similar medications, such as medication administration directed to geriatric, pediatric and oncology patients. Guidelines may also be included that are directed to particular therapy regimens, such as chemotherapy regimens or regimens for treating chronic infection or pain. In one embodiment of the present invention, the guidelines may include preestablished "hard" and "soft" limit values on physiological parameters (such as $CO_2$, $SpO_2$, respiration rate, and others), PCA dosing parameters, and other infusion and vital sign parameters.

As depicted in FIG. 2, the care management system is connected to other systems in the institution via an interface 10. This interface may support standard health level 7 (HL7) interfaces to the hospital's other information systems and can also support custom interfaces to systems or devices that do not support the HL7 standard. The system interfaces may be either real-time or batch mode, although a real-time interface to a hospital's pharmacy system may be required to support the on-line medical administration records keeping function of the medical administration management module 110.

The care management system software can be written to operate on a variety of operating systems to suit the needs of a variety of institutions. In a present embodiment, the software is written to interface with the nurses and physicians using the Windows environment (Windows is a trademark of Microsoft, Inc.) on IBM compatible micro-computers. The Windows environment is well known by those skilled in the art and will not be described in detail herein. The care management system software, when implemented using the Windows system, is particularly useful in that the Windows operating system provides the ability to load several programs at once. Multitasking programs, allowing several application programs to run simultaneously yet providing immediate access to the various software modules of the care management system may also be used.

One particular mode of operation of the care management system will now be described. As described above, a patient entering a hospital or other care-giving institution is provided with a wristband necklace, ankle band or other identifier that is affixed to the patient in a manner so that the patient can be identified even if the patient is unconscious or otherwise unresponsive. Such a wristband 170 is depicted in FIG. 4. In one embodiment, the wristband 170 barcode represents the name of the patient and other information that the institute has determined is important and also includes a barcode 175. The information printed upon the band, such as name, age, allergies or other vital information is encoded into the barcode 175. It will be understood, particularly in view of the description above, that the barcodes and wristbands may be replaced with devices capable of communicating with the various institution systems using devices capable of wireless communication with the institution's systems.

After the patient is admitted and situated in a bed within the institution, the patient is typically evaluated by a physician and a course of treatment is prescribed. The physician prescribes the course of treatment by preparing an order, which may request a series of laboratory tests or administration of a particular medication to the patient. The physician typically prepares the order by filling in a form or writing the order on a slip of paper to be entered into the hospital's system for providing care. Alternatively, the order may be entered into a terminal, computer, PDA or other device programmed to receive order information and communicate that information to the institution's pharmacy system.

If the order is for administration of a particular medication regimen, the order will be transmitted to the institution's pharmacy. The order will arrive in written or electronic form at the pharmacy, will be evaluated by the pharmacy, and processed. The pharmacy then prepares the medication according to the requirements of the physician. The pharmacy packages the medication in a container, such as the container 185 shown in FIG. 5. Normally, a copy of the order, or at a minimum, the patient's name, the drug name, and the appropriate treatment parameters are represented on a label that is then affixed to the drug container 185. According to one embodiment of the present invention, this information is represented by a barcode 182 that is then printed on a label 180. This barcode label 182 may be automatically generated using a printer capable of printing barcodes, such as, for example, a printer 69 attached to the hospital's pharmacy information system 20. The existence of this medication order is made available by the hospital's pharmacy information system 20 and is stored by the file server 45.

Generally, the medication is then delivered to the appropriate caregiving unit for administering to the patient. A nurse or technician carries the drug container 185 to the appropriate patient. In accordance with one embodiment of the present invention, the nurse or technician first reads the barcode 175 on the patient ID bracelet 170 using the barcode reader 90 connected to the bedside CPU 80. The nurse or technician would then read the barcode 182 on the label 180 affixed to the drug container by swiping the barcode wand 95 across the barcode 182 printed on the label 180 of the drug container 185. Additionally, a record of the identity of the caregiver dispensing the medication may be obtained by reading the barcode 205 printed on an identity badge 200 (FIG. 5A) typically worn by all institution personnel.

While the foregoing has been described with reference to the use of barcoded labels, those skilled in the art will also understand that passive identification devices such as those described above may be used to identify the patient, caregiver and medication to be administered. Such a system eliminates the need to read the barcodes and provides for relatively automatic identification and processing to determine if the right patient is being administered the right drug.

For certain drugs, the care-giver is prompted to enter data descriptive of a selected patient parameter or parameters, such a laboratory value or a current vital sign, before completing the verification process. For example, the care-giver may be prompted to measure and enter a value for a patient's blood pressure before administering certain selected drugs. The system may include ranges of acceptable values for the parameters. If the system detects an out-of-range value for the parameter, the system causes an alarm to be provided. In an alternative embodiment, the parameters could be monitored and entered into the system automatically, eliminating the need for manual entry by the care-giver.

The data obtained then is analyzed by the medication administration management module 110 which records the therapeutic regimen information in the patient's MAR, and verifies that the right medication is being given to the right patient in the right dose by the right route and at the right time. If the medication administration management module 110 detects a discrepancy between the barcoded information printed on the patient bracelet 170 and the barcoded information on the label 180 affixed to the medication container 185, an alert is sounded and the appropriate information is displayed on the video display 84 attached to the bedside CPU 80. The nurse or technician then either corrects the discrepancy by either re-reading the barcode 175 on the patient's bracelet 170 and the barcode 182 on the medication container 185 or, alternatively, by entering the appropriate information into the bedside CPU 80 using the keyboard 82 or touch screen 83, mouse, or other device. In the event that the nurse or technician determines that the discrepancy cannot be automatically corrected by re-reading the barcodes and that the discrepancy is minor and will not affect the accuracy or safety of the delivery of the medication, the nurse or technician may override the alert.

In an embodiment of the present invention, where the medication is to be delivered using an infusion pump, such as the infusion pumps 92 attached to the bedside CPU 80, the care management system automatically downloads information consisting of the appropriate configuration parameters for the infusion from the pharmacy CPU 60 through the local area network 50 into the bedside CPU 80 and then into the infusion pump 92 when the verification function of the medical administration management module 110 is complete. This is particularly advantageous in that one potential source of inaccuracy is eliminated by automatically configuring the pump, thus eliminating the need for the nurse or technician to manually enter the parameters necessary to configure the infusion pump 92. In one embodiment, the infusion pumps 92 comprise IVAC Corporation Model 570 volumetric pumps. In an embodiment where the pumps cannot be automatically configured by downloading parameters from the network, the care management system 30 only verifies that the right treatment is being administered to the right patient. The pump must then be manually configured by the physician, nurse, or technician.

Alternatively, the nurse or caregiver may enter values for various treatment parameters into the pump manually. In this embodiment, the pump, or other medication administration device, may have incorporated within a memory associated with the pump or medication device, a library or libraries of information such as institutional guidelines for appropriate parameters for administration for various medications or appropriate physiological parameters.

Once medication administration values have been entered into the patient care system or medication administration device by a nurse or other care-giver, the processor of the medication device is programmed to compare each of these selected values against the stored library to verify that the selected values are within acceptable ranges. If a selected value contravenes a hard limit, the processor will alarm and require a value change before operation of the medication administration device can begin. If the selected value contravenes a soft limit, the processor of the medication administration device will require an acknowledgment from the nurse or other care-giver that he or she understands the value entered is outside a soft limit and that this value is nevertheless to remain in force. The library or libraries may not necessarily be located in the medication administration system but may be located elsewhere. For example, in the case where patient care systems or medication administration devices are connected to a hospital server, such a library may be located at the hospital server and the patient care system or medication administration device would communicate with the server during the verification stage to obtain the acceptable ranges. In another embodiment, the library may be located in a portable data assistant (herein "PDA") such as a Palm Pilot™ with which the patient care system or medication administration device may communicate via infrared link, RF, blue tooth, or by other means. The nurse or care-giver may carry the PDA and before the patient care system or medication administration device will begin operation, it must communicate with the PDA to compare the hard and soft limits against the entered values. Other library arrangements are possible.

Storing a data base of institutional standards for drug infusion parameters and physiological parameter limits, such as the maximum and minimum concentrations of $CO_2$ and $SpO_2$ and the maximum and minimum values of respiration rate, also aids in standardizing the quality of care in a clinical setting. In some embodiments, infusion parameter values or physiological parameter limits may be entered automatically from a machine-readable label, for example using a bar code reader mounted on the bag or on the syringe or other medical fluid container in which the medical fluid to be infused is stored. In other embodiments, such infusion parameter values and physiological parameter values may also be entered by other means, such as through a connection with an external processor, such as a hospital server, through connection to a PDA, or other. Connections with these devices may be made in various ways, such as direct, hardwired connection, infrared link, blue tooth link, or others.

The medical database system of one embodiment of the present invention receives medication administration information from a nurse or care-giver prior to medication administration, compares that information to institutionally established guidelines for administration of various medications, and provides an alert if any or all of the medication administration information received from the medication administration device falls outside of the guidelines stored within the medical database. This allows the nurse or care-giver administering the medication to correct the administration parameters entered into the medication administration device before medication administration to the patient is begun. If the administration information falls within the guidelines, the nurse or care-giver may receive a message that medication administration may begin. In one embodiment, the medication administration device may be "locked out", that is, electronically prevented from beginning administration of the medication until the medication administration device receives a signal from the processor that the administration parameters entered into the administration device are appropriate for the medication and that institutional guidelines for the administration have been met, unlocking the medication administration device and allowing the care-giver to begin medication administration.

In another embodiment, a separate library or libraries may be stored, either in the medication administration device or at another location that contains records of the medication administration parameters and/or events. The information stored in the library or libraries may be communicated to and incorporated with information in other institutional information systems, such as a pharmacy information system, or hospital information system, event logging, analysis and reporting system, medical treatment data analysis system, or physician order entry system, or a patient specific asset located at a patient's bedside. The information stored in the library or libraries is used to validate that the right medication and the parameters of the medication administration record are properly delivered to the right patient. Additionally, in some embodiments, the information stored in the library or libraries may be analyzed and provided in a pre-established report format to the institution or care-giver to identify patterns and frequency of occurrence of logged events. In an alternative embodiment, the information stored in the library or libraries in communication with more than one medication administration device may be consolidated and analyzed, providing reports concerning the occurrence of events associated with selected areas within the institution, selected treatment protocols, or other categories as identified by the institution to assist the institution in ensuring the proper delivery of medication to patients within the institution.

In accordance with the present invention, a library or libraries of medical treatment data may be analyzed according to a selected treatment parameter for a plurality of patients for determining a medical treatment guideline representing acceptable values for the selected treatment parameter. Reports of the analysis may be provided to a technician or physician for creating or adjusting guidelines, or the system may automatically create or adjust medical treatment guidelines in accordance with the analysis.

A medical database in accordance with one aspect of the present invention may be a included in a device having a processor and a memory for storing information or databases, such as a personal data assistant ("PDA"), a laptop computer, a desktop computer, a smart card, a BLUETOOTH transceiver having a processor and memory, or other device capable of communicating with medication administration devices and storing and processing information. Such a medical data base carrier ("MDC") may either be portable, in the sense that the MDC may be moved about the institution, or the medical database carrier may be primarily stationary and located at the patient's bedside. At the patient's bedside, the medical database carrier is interfaced to a patient specific asset ("PSA"), such as an infusion pump or vital signs monitor.

Once the infusion pump or other medication administration device is configured, the nurse, caregiver, or technician starts the infusion by pressing the appropriate control on the infusion pump 92. Starting a pump that is capable of being monitored automatically by the care management system causes a signal to be transmitted from the pump to the bedside CPU 80 which is then logged by the clinical monitoring and event history module 130 and entered by the medical administration management module 110 into the patient's MAR. In the case where the institution is using a pump that is not capable of being configured by downloading parameters from the network, the nurse or other caregiver logs the start of the infusion using the touch screen device, mouse or other device connected to the bedside CPU 80. In this case, the video displays of the care management system that display information about the status of the infusion will not display real-time data. Rather, the care management system will project what the status of the infusion should be given the infusion parameters, the time elapsed since the infusion began, and any other events that were manually logged by the caregiver that may have affected the progress of the infusion.

The care management system, utilizing the application modules described above, monitors the infusion process in a real-time manner, providing alerts on the appropriate video display screens located throughout the institution and allows intervention by nurses or other caregivers at remote locations if necessary. If the pharmacy management system 20 is directly linked to the care management system, the care management system may also provide a scheduling report to the pharmacy in determining the status of ongoing infusions, as well as in scheduling the preparing of medications for future infusions.

In another embodiment, the present invention includes a "Code Mode" that allows a care-giver to bypass the system to immediately cause a list of drugs that have been preselected by the institution to be used in an emergency situation. The initiation of the "Code Mode" causes a time-stamp to be placed in the patient's MAR along with the identity of the drug selected from the displayed list of drugs to be used to treat the emergency. This feature ensures that the emergency and the treatment used to address the emergency are accurately recorded in the patient's MAR.

Figure 10:
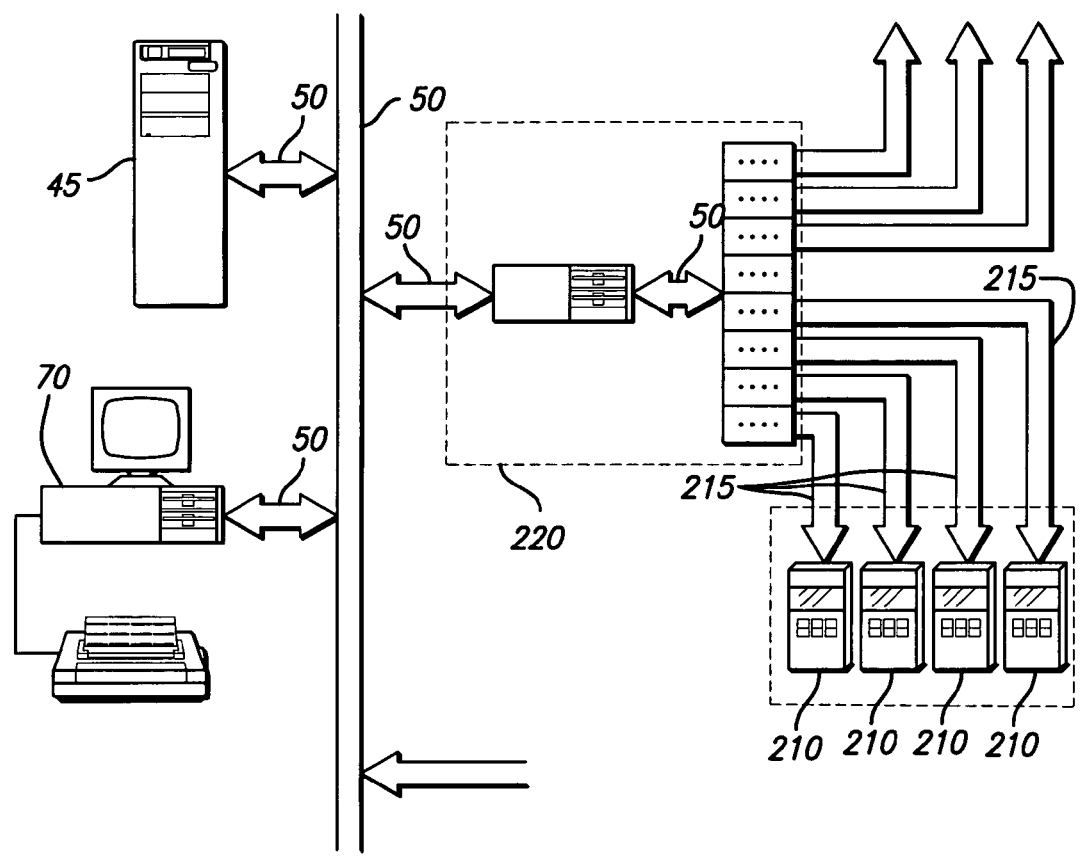
FIG. 10 is a graphical representation of another embodiment of the care management system showing the clinical devices connected to the local area network through a bedside data concentrator.

While one particular embodiment of the present invention has been described above, alternative configurations of the care management system network are possible. For example, one alternative embodiment of the care management system is depicted in FIG. 10. In this configuration, clinical devices 210 are connected by means of appropriate interfaces and cabling 215 to a bedside data concentrator 220 which would typically be located outside of a private room, semi-private room or ward area. In this configuration, there is no bedside CPU 80 as described previously. Instead, the bedside data concentrator 220 is connected through an appropriate interface and cabling to the local area network 50, where the data gathered from the clinical devices 210 is then available for processing by the care management system and display at the various monitoring stations, such as either in the pharmacy or at the nurse station 70. In this embodiment, there is no bedside CPU 80 having a keyboard 82 for data entry or a video display 84 for display of either clinical device information or patient information. As described previously, the devices may also communicate with each other and the communication system 50 by wireless means.

Figure 11:
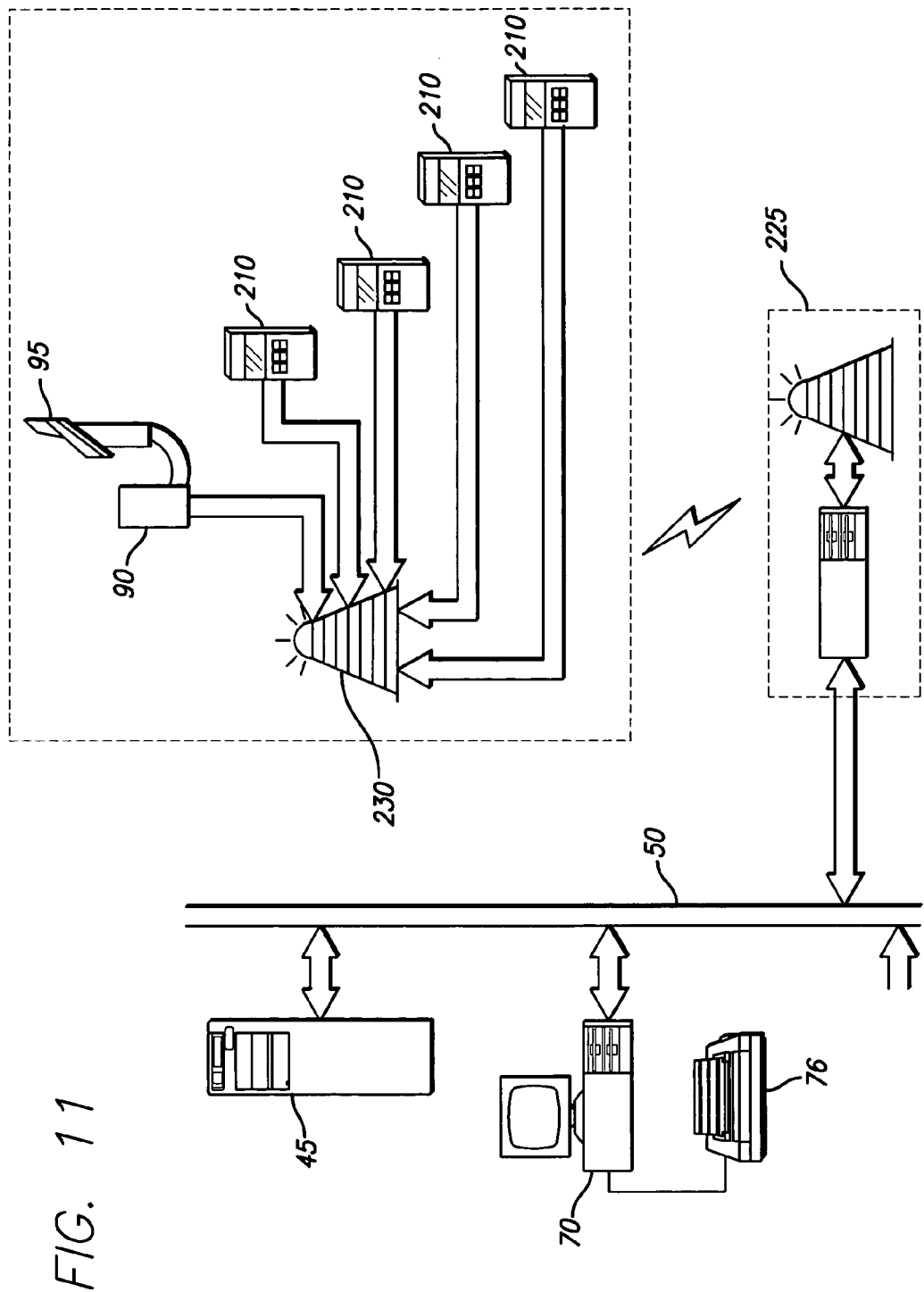
FIG. 11 is a graphical representation of still another embodiment of the care management system showing the clinical devices transmitting and receiving information from the local area network through RF transmitting/receiving equipment.

A further embodiment of the care management system local area network is depicted in FIG. 11. In this embodiment, the file server and monitoring stations are connected using appropriate interfaces and ethernet cabling to an RF data concentrator 225. At the bedside locations in the private rooms, semi-private rooms or ward areas of the institution, the clinical devices 210 and barcode reader 90 at the bedside are connected to an RF transmitter/receiver 230. This RF transmitter/receiver 230 transmits the information gathered from the clinical devices 210 and the barcode reader 90 to the RF data concentrator 225 attached to the local area network 50. Thus, expensive cabling is not required to connect every patient treatment area. Additionally, flexibility in locating the clinical devices 210 and barcode reader 90 is obtained as well as allowing the ability to reconfigure the patient treatment area without costly rewiring of the ethernet cabling.

Figure 12:
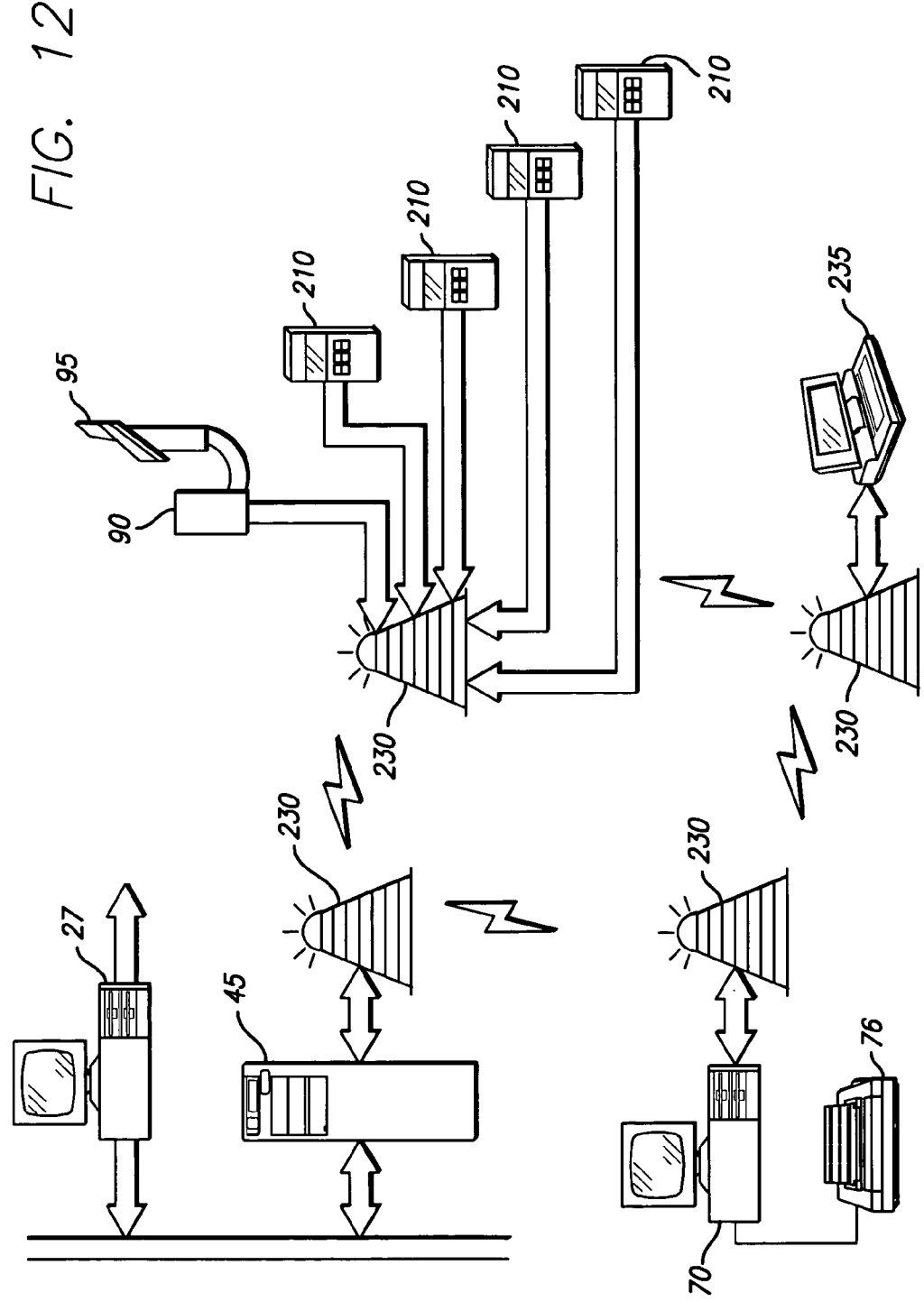
FIG. 12 is a graphical representation of another embodiment of the care management system of the present invention where all of the hardware elements of the local area network communicate with each other using RF transmitting/receiving equipment.
Figure 13:
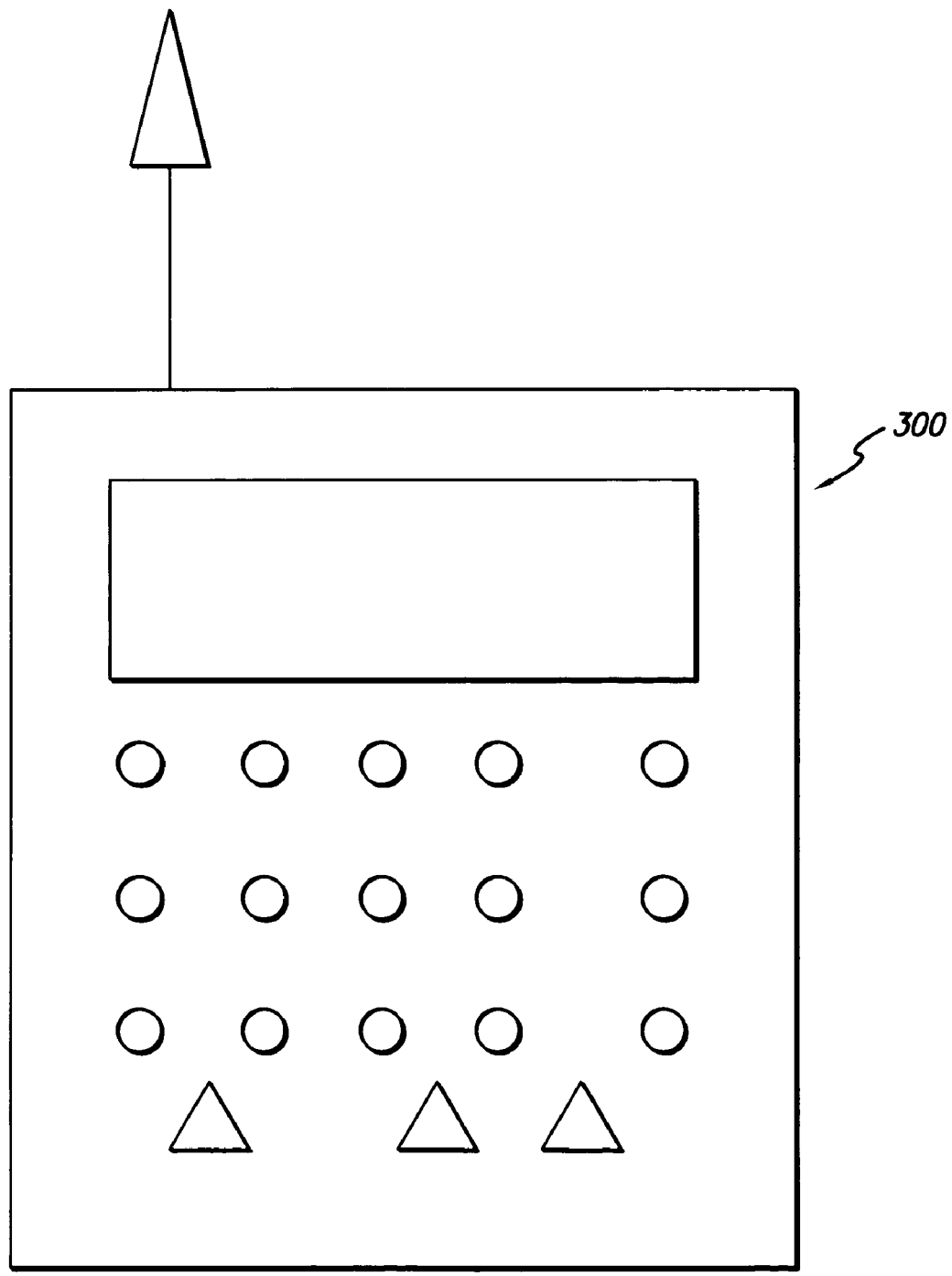
FIG. 13 is a graphical representation of another embodiment of the care management system of the present invention wherein a library or libraries of various patient treatment related information are stored in the memory of a medication database carrier which may be configured to communicate with an institutions systems using either a hard wired or wireless communication system.

Yet another embodiment of the care management system local area network 50 configuration is shown in FIG. 12. In this configuration, the ethernet cabling connecting the pharmacy CPU, the nurse station nursing CPU 70 and bedside CPUs and clinical devices is eliminated entirely. Each hardware element, comprising the file server, nursing CPU 70, pharmacy CPU 60 and bedside CPUs 80 and clinical devices and/or barcode readers is connected to an RF transmitter/receiver 230. In this manner, all of the information is transmitted throughout the local area network 50 by way of radio transmission rather than by using costly network cabling. Such a system would additionally allow for the use of portable computers 235, PDAs, smart cards and other devices, such as portable medication data carriers, described more fully below, having RF transmitter/receivers 230 or other means of wireless communication, as have been described above, that could then be carried with physicians, nurses or technicians as they circulate through the institution. With this configuration, caregiving personnel could access the care management system either spontaneously or upon notification of an alert no matter where they were in the institution at any given time. Such a system would be particularly useful in a large institution where caregiving personnel are likely to be responsible for many hospital beds or when personnel are out of the area or off the floor. In accordance with aspects of the present invention, a medication database carrier ("MDC") 300, one embodiment of which is depicted in FIG. 13, including a processor and a memory for storing information is provided to monitor medication parameters or other information used by a nurse or other care-giver to program a medication administration device to deliver medication to a patient. Various types of information may be stored in the memory of the MDC 300, including databases containing information about drug interactions and possible contraindications and/or side-effects of medications, and a library or libraries of established guidelines for the administration of various medications. For example, the guidelines may include institutionally-established guidelines or limits on drug administration parameters, such as dosage, frequency of administration, and other delivery related information such as, for example, appropriate flow rates and infusion durations for programming infusion pumps. Additionally, the guidelines may encompass guidelines for providing drug administration appropriate to a particular patient or to treatment areas having different sets of delivery parameters for similar medications, such as medication administration directed to geriatric, pediatric, and oncology patients. Guidelines may also be included that are directed to particular therapy regimens, such as chemotherapy regimens or regimens for treating chronic infection or pain. The term "database" or "data base" as used herein will be understood by those skilled in the art to be used as is commonly understood, that is, the term "data base" refers to a collection of values or information organized, formatted, and stored in such a manner as to be capable of being retrieved and analyzed using an appropriate program contained in software or other form.

In one embodiment of the present invention, the MDC 300 may be interfaced to the nurse station computer system 70 (FIG. 2) or any other of the information systems of the central system of an institution through a cradle or other docking device that provides a connection between the MDC 300 and the care management system. This information may then be processed and stored on the care management system, or the information may be communicated by the care management system to various other institutional information systems over the communication system 50. In this manner, information from the pharmacy information system 20, for example, may be communicated through the communication system 50, the nurse station computer system 70, and the MDC cradle into the MDC 300. Similarly, information contained within the MDC 300 may be communicated through the MDC cradle, the nurse station computer system 70, and the communication system 50 to any of the interconnected systems 4, 20, 40, 42 and 49. Alternatively, the MDC may be capable of wireless communication with any or all of the interconnected systems 4, 20, 40, 42 and 49, or any other institutional system.

The medical database carrier 300 generally refers to a device that contains medication and/or patient specific information and/or databases or libraries, including institutionally generated guidelines for the delivery of medication to a patient, as well as drug interaction information or information concerning possible drug side-effects, and that is portable such that it can be carried by a nurse or other care-giver to and from a patient's bedside. Alternatively, as will be described in more detail below, the MDC 300 may be considered to be relatively stationary in that it is associated with either a particular patient or medication administration device. The MDC 300 may also have a storage capability and technology for interfacing with a computer system or network so that information may be communicated between the MDC 300 and other devices, such as computers, medication administration devices, clinical devices such as vital signs monitoring devices and the like. The MDC may also have a video display screen in color or black and white (mono-color), such as that provided by an LCD or an array of LED's, or other, and a data entry means such as a keyboard, keypad, a screen used for handwriting recognition, or other data entry means.

A general concept embodied in the MDC 300 is to provide a system and method wherein medication administration parameters or other information entered into a medication administration device such as an infusion pump, may be retrieved from the device prior to actual medication administration and compared to information in the database or databases stored in the MDC to determine if the entered parameters or information fall within institutionally established guidelines for the administration of a particular medication. If the comparison indicates that the parameters or information entered into the medication administration device are appropriate in that they fall within the established guidelines, then an indication to that effect is provided to the nurse or care-giver and the nurse may then begin medication administration.

Alternatively, if the comparison indicates that one or more parameters or information do not meet the established guidelines, a warning or alert is provided to the nurse or care-giver that one or more parameters or a portion of information has been incorrectly entered into the medication administration device, and that corrective action or an override is required before medication administration can begin. In another embodiment, the medication administration device may be automatically inhibited from starting administration of a medication unless it receives a signal from the MDC 300 that the comparison was favorable, thus providing a fail-safe against incorrect administration of the medication.

The MDC 300 typically will also be capable of retrieving medication administration parameters or information from a medication administration device, and storing data or information concerning various transactions in its memory representing the identity and treatment regimens for medications given to a patient, as well as other information, such as care-giver identity, equipment location, patient vital signs information, or any other information sought to be recorded. The MDC 300 may also store data or information concerning primary or secondary validation of previous and/or duplicate transactions of medical treatment information. The display of the MDC may also provide a care-giver with messages or other information, such as warnings or prompts to enter data, related to medication administration. Moreover, the keyboard or other information entry means of the MDC may be used for manually entering information into the MDC for storage in the memory of the MDC.

While specific examples of an MDC 300 are set forth herein, it will be understood that the MDC is meant to include any device that carries out the basic concept of the invention. That is, a device that receives medication administration or treatment information from a medication administration device, such as, for example, but not limited to, an infusion pump, and has a processor capable of comparing the received information to institutionally established medication administration guidelines or other pertinent information or data, such as drug interaction information and/or a library of possible side-effects, and then providing an indication of the result of the comparison to a nurse or care-giver before administration of a medication to a patient is begun, will accomplish the aims of the present invention. A particularly advantageous embodiment includes storing information about the medication administration, such as the medication administration or treatment parameters, and/or other information, such as the identity of the patient and care-giver, in the memory of the MDC 300 until the MDC 300 re-establishes a communication connection with the care management system, whereby the information stored in the memory of the MDC 300 may be communicated to the care management system and incorporated into one or more of an institution's information databases. Updating the databases provides a verification that the treatment has been rendered thereby avoiding a duplicate treatment. In this manner, the present invention "closes the loop" ensuring that the right medication has been given in the right manner to the right patient.

For example, consistent with the present invention, the MDC 300 may be embodied in a hand-held "personal digital assistant" ("PDA") such as a Palm™ Pilot or any PDA running either the Palm™ operating system or the Windows™ operating system, a desktop computer, a notebook computer, or other portable computer system. The MDC may also comprise a smartcard such as those that are capable of processing and storing data, such as the American Express Bluecard. The use of such devices is advantageous in that devices having a suitably large memory to accommodate the type of information required by the present invention to monitor and track medication administration information and validate treatment as well as retrieving other patient information, are readily available and relatively inexpensive, thus allowing an MDC to be assigned to each individual patient, or alternatively, to an individual medication administration device, such as an infusion pump, or other clinical device, such as a vital signs monitor. Additionally, such devices are small, compact and easily transportable.

Alternatively, the MDC 300 may be embodied in any device that includes an active embedded processor and a memory capable of storing information. Such an active embedded processor may be even smaller and more portable than a PDA or notebook computer. For the purposes of the present invention, such an active embedded processor includes any device incorporating a microprocessor and allows for input and/or output of information, whether via electrical, radio frequency, or optical means, wireless or direct contact, and which contains its own power supply. One example of an active embedded processor in accordance with this invention may be attached to or embedded in the packing or container of a medication to be delivered to a patient. Such devices may typically be manufactured no larger than, for example, a postage stamp or business card and yet include, using micro circuitry, enough processing power, information storage, data or information input and output, and power to be suitable for use as a medical database carrier. Alternatively, the embedded processor and memory may be integrated into a medication administration device, such as an infusion pump or other device.

In another embodiment, such as where the patient specific asset or medication administration device is modular and includes an point of care unit "PCU"), such as in the ALARIS Medical Systems, Inc. MEDLEY™ MEDICATION SAFETY SYSTEM, the PCU may include sufficient programming to perform the function of an MDC. In such case, the PCU would be in contact with institutional information systems, such as the pharmacy information system 20, and receive updated information concerning institutional guidelines for medication administration or other patient area or drug specific information to be used to compare with entered medication administration information or parameters before beginning administration of a medication to a patient.

It is not unusual at present to find patient stations having a computer 80 (FIG. 2) located at patient bedsides in a care-giving facility. Such stations 80 may serve a single patient, or may serve more than one patient, depending on the design and arrangement of the patient area. There may also be a variety of equipment or clinical devices attached to the bedside computer 80. Examples of such devices are a bar code reader 90, a printer (not shown), patient monitoring equipment 94 for monitoring patient vital signs, or other patient specific assets assigned to the patient. Further examples of such PSA's include an infusion device 92 such as can form a part of the ALARIS Medical Systems, Inc.'s MEDLEY™ MEDICATION SAFETY SYSTEM 80. Attention is directed to U.S. Pat. No. 5,713,856 entitled "Modular Patient Care System" to Eggers et al. in which the PCU is described as an advanced interface unit, and is incorporated herein by reference. In such system, an infusion device may be mounted to an Advanced Programming Module. Other devices, such as a vital signs monitor or monitors, are envisioned as being mountable to the PCU also. Other infusion or drug delivery devices and/or patient monitoring equipment such as cardiac or respiratory monitors may also comprise or form a part of the PSA.

The bedside equipment and clinical devices are typically equipped with data communication technology such as RS 232 serial ports or proprietary communication ports that allow information and data to be communicated to and from the equipment or clinical device. Using this communication technology, the bedside equipment and clinical devices may be connected to the bedside computer 80, or, alternatively, they may be connected, either by wire or wireless system, to the facility communication system 30 using wireless technology, such as RF, IR, or other wireless communication protocols.

As described previously, one particularly advantageous embodiment of the present invention includes an MDC 300 (FIG. 13) that is capable of communicating information to and from the a medication administration device and the institution' communication network 50 using wireless technology. For example, the MDC 30 may be understood to include, but is not limited to, communications utilizing optical or infrared transmission, magnetic transmission, or wireless technology where the wireless technology is understood to include methodology such as the BLUETOOTH™ technology (IEEE 522.15), standard methodologies such as wireless Internet, WAP or any other proprietary communication scheme using electromagnetic waves instead of wires to connect and communicate between devices. Such wireless communications may also be performed using other wireless networking alternatives, such as those described in the IEEE 522.11x standards. Wireless technologies are designed to create wireless networks allowing devices such as PDA's, cell phones, and personal computers to exchange information at relatively high transmission speeds.

Using BLUE TOOTH™ technology, for example, data from a medication administration device such as an infusion pump may be sent by an internal BLUE TOOTH™ communication device taking the form of a radio chip embedded in the medication administration device to a similarly equipped MDC 300 or, alternatively, to a mobile telephone transmitter/receiver for transmission to a receiver connected to a server system. Using the IEEE 522.11x standards for example, data is transmitted directly to a receiver, which may be wired into a network using Ethernet or other network topology. The MDC of the present invention may be capable of wireless communication using either BLUE TOOTH™ or other technologies (such as those described in IEEE 522.11x), and may be used throughout a care giving facility without the disadvantage of requiring cumbersome hardwired devices.

While the medication administration device described above was primarily described in terms of an infusion pump, devices incorporating the principles of the present invention may also be a vital signs monitor or other clinical device interacting with a patient. For example, the medication administration device may also be a patient feeding device.

Furthermore, the institutional communication systems 5 and 50 as mentioned above numerous times are not meant to be taken in a limited sense. Such a communication system may encompass an entire hospital facility or may be located only in a small area of the hospital. It may also include a communication system in a care-giving facility other than a hospital and may have application to an alternate care facility, such as a patient's home. The above embodiments are described for exemplary purposes only.

In the above detailed description, well-known devices, methods, procedures, and individual components have not been described in detail so as not to obscure aspects of the present invention. Those skilled in the art will understand those devices, methods, procedures, and individual components without further details being provided here. Moreover, while the embodiments disclosed above are described for use in a hospital environment, it will be understood that the system and method may be useful in other environments as well, such as outpatient clinics and other environments where care is delivered to a patient.

While several specific embodiments of the invention have been illustrated and described, it will be apparent that various modifications can be made without departing from the spirit and scope of the invention. Accordingly, it is not intended that the invention be limited, except as by the appended claims.

I claim:

1. A system for analyzing medical treatment data associated with medical treatments for a plurality of patients to determine a medical treatment guideline based on actual treatment of a plurality of patients, and for updating at least one medical device that is in communication with the system with the guideline, the system comprising:
   a memory for storing medical treatment data associated with medical treatments actually delivered to a plurality of patients, the medical treatment data including a plurality of treatment parameters for each of the plurality of patients and a treatment parameter value associated with each treatment parameter; and
   a processor operatively connected to the memory and configured to compile from the medical treatment data a plurality of treatment parameter values associated with a selected treatment parameter, analyze the compiled treatment parameter values, and determine a medical treatment guideline in accordance with the analysis, the medical treatment guideline representing acceptable values for the selected treatment parameter, and to automatically supply the medical device with at least one revised treatment guideline.

2. The system of claim 1 wherein the analysis of the compiled treatment parameter values includes providing a statistical distribution of the compiled treatment parameter values.

3. The system of claim 1 further comprising:
   a database for storing preestablished medical treatment guidelines; and
   wherein the processor is further configured to compare the compiled treatment parameter values to the acceptable values for the treatment parameter in the corresponding preestablished medical treatment guideline for the selected parameter.

4. The system of claim 3 wherein the processor is further configured to adjust the acceptable values for the selected treatment parameter in the preestablished medical treatment guideline as a result of the comparison to create an updated medical treatment guideline for the selected treatment parameter.

5. The system of claim 3 wherein the processor is further configured to generate a report of the comparison.

6. The system of claim 1 wherein the processor is further configured to generate a report of the analysis.

7. The system of claim 1 wherein the processor is further configured to integrate the determined medical treatment guideline into a database of preestablished medical treatment guidelines.

8. The system of claim 1 wherein the processor is further configured to determine a medical treatment guideline in accordance with the analysis, the medical treatment guideline representing an optimum value for the selected parameter.

9. The system of claim 1 wherein the medical treatment data includes patient physiological data, and the processor is further configured to analyze the treatment parameter values of the selected treatment parameter with respect to the corresponding physiological data for each of the plurality of patients and to determine a medical treatment guideline in accordance with the analysis, the medical treatment guideline representing at least one optimum value for the selected treatment parameter.

10. A system as described in claim 1, wherein the medical device is an infusion pump.

11. A system for analyzing medical treatment data to determine medical treatment guidelines associated with medication delivered to a patient by a medication administration device, the system comprising:
   a plurality of medication administration devices for delivering medication to a plurality of patients;
   a memory associated with each medication administration device for storing medical treatment data associated with the medication actually delivered to each of the plurality of patients, the medical treatment data including patient identification data, medication identification data and medication administration device operating parameters;
   a central processor configured to receive medical treatment data from each of the medication administration devices;
   a database operatively connected to the central processor for storing preestablished medical treatment guidelines representing acceptable values for the medical administration device operating parameters;
   means for communicating medical treatment data from the medication administration device to the central processor; and
   means to update treatment guidelines in the medical devices;
   wherein the processor is configured to compile from the medical treatment data a plurality of parameter values associated with a selected medication administration device operating parameter, analyze the compiled parameter values, and determine a medical treatment guideline in accordance with the analysis, the medical treatment guideline representing acceptable values for the selected parameter.

12. A system as described in claim 11, wherein the means to update treatment guidelines in the medical devices comprises means to automatically update the treatment guidelines in the medical devices.

13. A method for analyzing medical treatment data associated with medical treatments for a plurality of patients to determine a medical treatment guideline, the method comprising:
   communicating medical treatment data associated with medical treatments actually delivered to a plurality of patients, the medical treatment data including a plurality of treatment parameters for each of the plurality of patients and a treatment parameter value associated with each treatment parameter;
   compiling from the medical treatment data a plurality of treatment parameter values associated with a selected treatment parameter;
   analyzing the compiled treatment parameter values;
   determining a revised medical treatment guideline in accordance with the analysis, the medical treatment guideline representing acceptable values for the selected treatment parameter; and
   providing the revised medical treatment guideline to a medical device from a remote location.

14. The method of claim 13 wherein analyzing the treatment parameter values includes providing a statistical distribution of the treatment parameter values for the selected treatment parameter.

15. The method of claim 13 further comprising:
   storing preestablished medication treatment guidelines in a database; and
   comparing the compiled treatment parameter values to the acceptable values for the treatment parameter in the corresponding preestablished medical treatment guideline for the selected parameter.

16. The method of claim 15 further comprising:
   adjusting the acceptable values for the selected treatment parameter in the preestablished medical treatment guideline as a result of the comparison to create an updated medical treatment guideline for the selected treatment parameter.

17. The method of claim 15 further comprising:
   generating a report of the comparison.

18. The method of claim 13 further comprising:
   generating a report of the analysis.

19. The method of claim 13 further comprising:
   integrating the determined medical treatment guideline into a database of preestablished medical treatment guidelines.

20. The method of claim 13 further comprising:
   determining a medical treatment guideline in accordance with the analysis, the medical treatment guideline representing an optimum value for the selected parameter in accordance with the analysis.

21. A system for analyzing medical treatment data associated with medical treatments for a plurality of patients to determine a medical treatment guideline based on actual treatment of a plurality of patients, the system comprising:
   a memory for storing medical treatment data associated with medical treatments delivered to a plurality of patients, the medical treatment data including a plurality of treatment parameters for each of the plurality of patients and a treatment parameter value associated with each treatment parameter;
   a processor operatively connected to the memory and configured to compile from the medical treatment data a plurality of treatment parameter values associated with a selected treatment parameter, analyze the compiled treatment parameter values, and determine a medical treatment guideline in accordance with the analysis, the medical treatment guideline representing acceptable values for the selected treatment parameter; and
   a medication device having an alarm and a library of appropriate parameters, the alarm being activated when a medical treatment guideline having parameters outside of the appropriate parameters is input into the medication device.

* * * * *